(12) United States Patent
Musicki

(10) Patent No.: US 7,365,071 B2
(45) Date of Patent: Apr. 29, 2008

(54) HETEROCYCLIC COMPOUNDS, PREPARATION PROCESS AND INTERMEDIATES, AND USE AS MEDICAMENTS, IN PARTICULAR AS β-LACTAMASE INHIBITORS AND ANTIBACTERIALS

(76) Inventor: Branislav Musicki, 4 rue de Louvois, 75002 Paris (FR)

( * ) Notice: Subject to any disclaimer, the term of this patent is extended or adjusted under 35 U.S.C. 154(b) by 113 days.

(21) Appl. No.: 10/655,364

(22) Filed: Sep. 4, 2003

(65) Prior Publication Data
US 2004/0097490 A1 May 20, 2004

(30) Foreign Application Priority Data
Sep. 5, 2002 (FR) .................................. 02 10957

(51) Int. Cl.
| A61P 31/00 | (2006.01) |
| A61K 31/4995 | (2006.01) |
| C07D 237/28 | (2006.01) |
| C07D 243/02 | (2006.01) |
| C07D 487/08 | (2006.01) |
| C07D 235/00 | (2006.01) |

(52) U.S. Cl. ...................................... 514/248; 544/234
(58) Field of Classification Search ................ 514/248; 544/234
See application file for complete search history.

(56) References Cited

U.S. PATENT DOCUMENTS

| 5,932,587 | A | 8/1999 | Schmeck et al. ............ 514/278 |
| 6,350,733 | B1 | 2/2002 | Klich et al. .................... 514/27 |
| 6,420,538 | B1 | 7/2002 | Haesslein et al. .............. 536/8 |
| 6,579,902 | B1 | 6/2003 | Demassey et al. .......... 514/456 |
| 6,583,119 | B2 | 6/2003 | Haesslein et al. ............. 514/27 |
| 6,812,331 | B2 | 11/2004 | Klich et al. ................. 536/16.8 |
| 2004/0157826 | A1 | 8/2004 | Lampilas et al. ...... 514/214.03 |
| 2005/0245505 | A1 | 11/2005 | Aszodi et al. ......... 514/214.03 |
| 2007/0191312 | A1 | 8/2007 | Musicki ....................... 514/80 |

FOREIGN PATENT DOCUMENTS

| EP | 0702004 | 3/1996 |
| EP | 0818197 | 1/1998 |
| EP | 1227090 | 7/2002 |
| EP | 1798231 | 6/2007 |
| FR | 2676230 | 11/1992 |
| JP | 05-339263 | 12/1993 |
| JP | 5339263 | 12/1993 |
| WO | WO 90/15058 | 12/1990 |
| WO | WO 95/09175 | 4/1995 |
| WO | WO 95/18129 | 7/1995 |
| WO | WO 96/29327 | 9/1996 |
| WO | WO 97/23484 | 7/1997 |
| WO | WO 99/01434 | 1/1999 |
| WO | WO 99/16442 | 4/1999 |
| WO | WO 99/52875 | 10/1999 |
| WO | WO 00/00479 | 1/2000 |
| WO | WO 00/12507 | 3/2000 |
| WO | WO 00/37458 | 6/2000 |
| WO | WO 00/63187 | 10/2000 |
| WO | WO 01/25228 | 4/2001 |
| WO | WO 01/79206 | 10/2001 |
| WO | WO0210172 | 2/2002 |
| WO | WO 02/067937 | 9/2002 |
| WO | WO 02/100860 | 12/2002 |
| WO | WO 03/063864 | 8/2003 |
| WO | WO 2004/022563 | 3/2004 |
| WO | WO 2004/052891 | 6/2004 |

OTHER PUBLICATIONS

Ames D E et al, Cinnolines. II. The structures of N-methylcinnolones, J. Chem. Soc., 1963, 4924-9, pp. 4928.
Groszkowski Stefan et al., Synthesis of new derivatives of [1,2,5]triazepino[1,2-a]cinnoline. I. Synthese of 4-oxo-1,2,3,4-tetrahydrocinnoline hydrochlorides, Acta Poloniae Pharmaceutica, 1989, 46(4), pp. 320-326.
Hall H. K. Jr. et al., 3-Isopropyl-1,3-diazabicylo[3.3.1]nonan-2-one, a Simple Bicyclic Urea with a Bridgehead Nitrogen Atom, Journal of Organic Chemistry, 1972, vol. 37(5), pp. 697-699.
Hall H. K. Jr. et al., Anti-Bredt Bridgehead Nitrogen Compounds in Ring-Opening Polymerization, Chemical Reviews, 1983, vol. 83(5), pp. 549-555.
Hall H. K. Jr. et al., Anti-Bredt Molecules. 3.1a 3-Oxa-1-azabicyclo[3.3.1]nonan-2-one and 6-Oxa-1-azabicyclo[3.2.1]octan-7-one, Two Atom-Bridged Bicyclic Urethanes Possessing Bridgehead Nitrogen, J. Org. Chem., 1980, vol. 45(26), pp. 5325-5328.
Nicolaou K C et al., New Synthetic Technology for the Rapid Construction of Novel Heterocycles—Part 2. The Reaction of IBX with Anilides and Related Compounds, Agnew. Chem. Int. Ed., 2000, vol. 39(3) pp. 625-628.
Stanczak Andrzej, Synthesis of N-benzyl-4-oxo-1,2,3,4-tetrahydrocinnolines, Acta Poloniae Pharmaceutica, 1997, 54(5), pp. 381-387.
International Search Report from PCT Application No. PCT/FR 03/02639 (as published in WO04/022563), dated Feb. 23, 2004 (4 pages).

(Continued)

*Primary Examiner*—Brenda L Coleman
(74) *Attorney, Agent, or Firm*—Harnes, Dickey & Pierce, P.L.C.

(57) ABSTRACT

The invention relates to novel heterocyclic compounds of general formula (I) and to their salts with a base or an acid:

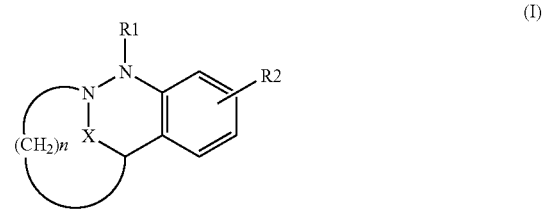

(I)

The invention also relates to processes and to intermediates for the preparation of these compounds, and to their use as medicaments, in particular as antibacterials and β-lactamase inhibitors.

17 Claims, No Drawings

OTHER PUBLICATIONS

International Search Report from PCT Application No. PCT/FR 02/01877 (as published in WO02/100860), dated Mar. 10, 2003 (27 pages).

International Search Report from PCT Application No. PCT/FR 03/03523 (as published in WO04/052891), dated Mar. 29, 2004 (12 pages).

Booker-Milburn, K.I. et al., "Azabenzocycloheptenones. Part 20. Synthesis and utilisation of 4-amino-1,2,3,4-tetrahydro-1(1H)-benzazepines," J. Chem. Soc., Perkin Trans. 1: Organic and Bio-Organic Chemistry, pp. 3261-3273 (1997).

Elliott, R. et al., "Syntheses and stereochemistry of 4-hydroxy tetrahydroisoquinolines in the 1-benzyl and 1-phenethyl series. Efficient routes to isopavines and homoisopavines," Tetrahedron Letters, vol. 21, pp. 4633-4636 (1980).

Heier, R.F. et al., "An asymmetric synthesis of (R)-5,6-dihydro-5-(methylamino)-4H-imidazo-[4,5,1-ij]quinolin-2(1H)-one and its [2-14C]- and [6,7-3H2]-labeled forms," J. of Labelled Compounds and Radiopharmaceuticals, vol. 38(12), pp. 1087-1098 (1996) (Abstract only from Chemical Abstracts Service).

Heier, R.F. et al., "Synthesis and Biological Activities of (R)-5,6-Dihydro-N,N-dimethyl-4H-imidazo[4,5,1-ij]quinolin-5-amine and Its Metabolites," J. Med. Chem., vol. 40, pp. 639-646 (1997).

Moon, M.W. et al., "Dopaminergic and Serotonergic Activities of Imidazoquinolinones and Related Compounds," J. Med. Chem., vol. 35, pp. 1076-1092 (1992).

Moon, M.W. et al., "Medicinal chemistry of imidazoquinolinone dopamine receptor agonists," Drug Design and Discovery, vol. 9(3-4), pp. 313-322 (1993) (Abstract only from Chemical Abstracts Service).

Moon, M.W. et al., "Synthesis of tritium-labeled (R)-5-(di[2,3-3H2]propylamino)-5,6-dihydro-4H-imidazo-[4,5,1-ij]quinolin-2(1H)-one([3H]U-86170) and (R)-5-([2,3-3H2]propylamino)-5,6-dihydro-4H-imidazo-[4,5,1-ij]quinolin-2(1H)-one([3H]U-91356)," J. of Labelled Compounds and Radiopharmaceuticals, vol. 31(11), pp. 933-943 (1992) (Abstract only from Chemical Abstracts Service).

Pennington, F.C. et al., "Preparation and cyclization of substituted 1-anilino-3-halo-2-propanols and their conversion to indoles," J. of Org. Chem., vol. 30(8), pp. 2801-2804 (1965) (Abstract only from Chemical Abstracts Service).

Romero, A.G. et al., "Oxidative Cyclization of Acyclic Ureas with Bis(trifluoroacetoxy)iodobenzene to Generate N-Substituted 2-Benzimidazolinones," Tetrahedron Letters, vol. 37, No. 14, pp. 2361-2364 (1996).

Shiotani, S. et al., "Studies on Diazabenzobicyclo[3.3.1]nonane System. I. Synthesis of 3,4,5,6-tetrahydro-2H-1,5-methanobenzo[g]-[1,4]diazocine and its Derivatives," Chem. Pharm. Bull., vol. 12, No. 6, pp. 647-651 (1964).

Tirk, I. et al., "Hydroxyiminoisoquinolin-3(2H)-Ones, VI: Synthesis and Biological Activity of Some Aminoisoquinoline Derivatives," Acto Chimica Hungarica, vol. 124, No. 2, pp. 195-207 (1987).

Triebs, W. et al., "Experiments for the preparation of azatropolones. I. Disubstituted 1-aza-4,5-cycloheptanedione and 5-azatropolone," Journal fuer Praktische Chemie (Leipzig), vol. 14, pp. 208-217 (1961) (Abstract only from Chemical Abstracts Service).

Zhou, B. et al., "Studies Directed to the Total Synthesis of ET 743 and Analogues Thereof: An Expeditious Route to the ABFGH Subunit," Org. Lett., vol. 4, No. 1, pp. 43-46 (2002).

HETEROCYCLIC COMPOUNDS, PREPARATION PROCESS AND INTERMEDIATES, AND USE AS MEDICAMENTS, IN PARTICULAR AS β-LACTAMASE INHIBITORS AND ANTIBACTERIALS

CROSS-REFERENCE TO RELATED APPLICATIONS

This application claims the benefit of priority from French Patent Application 02 10957, filed Sep. 5, 2002.

SUMMARY OF THE INVENTION

The invention relates to novel heterocyclic compounds, to their preparation and their use as medicaments, in particular as β-lactamase inhibitors and antibacterials.

BACKGROUND OF THE INVENTION

The preparation of a bicyclic derivative of empirical formula $C_{10}H_{18}N_2O$ is disclosed in J. Org. Chem., Vol. 37, No. 5, 1972, pages 697 to 699.

The preparation of bicyclic derivatives of empirical formulae $C_6H_9NO_2$ and $C_7H_{11}NO_2$ is disclosed in J. Org. Chem., Vol. 45, No. 26, 1980, pages 5325-5326.

The preparation of bicyclic derivatives of empirical formulae $C_{10}H_{18}N_2O$ and $C_7H_{12}N_2O$ is disclosed in Chemical Reviews, 1983, Vol. 83, No. 5, pages 549 to 555.

The preparation of a compound of empirical formula $C_{12}H_{12}N_2O$ is disclosed in Angew. Chem. Int. Ed., 2000, 39, No. 3, pages 625 to 628.

No specific therapeutic use of these compounds was disclosed in these documents.

French patent application No. 2 812 635 discloses that variously substituted heterocyclic compounds, in particular of the 7-oxo-1-aza- or 1,6-diazabicyclo[3.2.1]octane type, exhibit antibacterial properties.

DETAILED DESCRIPTION OF THE INVENTION

The present invention relates to compounds of formula (I):

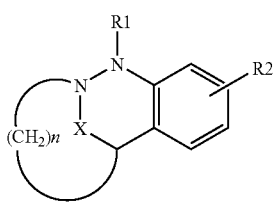

in which:
n is 1 or 2;
$R_1$ is selected from the group consisting of hydrogen, alkyl having up to 8 carbon atoms and $(CH_2)_{n'}R°_1$ in which n' is 0 or 1 and $R°_1$ is selected from the group consisting of aryl having up to 12 carbon atoms; heteroaryl having up to 15 carbon atoms and at least one heteroatom selected from N, S, and O; COR'; CONR'R"; CSNR'R"; COCOOR'; $SO_2NR'R"$; $SO_2R'$; $CO_2R'$ and CN;

R' is selected from the group consisting of hydrogen, alkyl having up to 8 carbon atoms, alkenyl having up to 8 carbon atoms, aralkyl having up to 12 carbon atoms and aryl having up to 12 carbon atoms;

R" is selected from the group consisting of hydrogen; alkyl having up to 8 carbon atoms; aryl having up to 12 carbon atoms; aralkyl having up to 12 carbon atoms; $SO_2$—R' and COR'; in each case R' being independently selected from the group consisting of hydrogen, alkyl having up to 8 carbon atoms, alkenyl having up to 8 carbon atoms, aralkyl having up to 12 carbon atoms and aryl having up to 12 carbon atoms;

$R_2$ is selected from the group consisting of hydrogen, halo, alkyl, OH, Oalkyl, $NO_2$, $NH_2$, NHalkyl, $N(alkyl)_2$, NHCOalkyl, $NHSO_2$alkyl, CONHalkyl, $SO_2$NHalkyl, COOH, COOalkyl, CN, $OSO_2$alkyl, NHCONHalkyl and COalkyl; said alkyl having up to 8 carbon atoms;

X is a divalent group —C(O)—N(OR₃)— connected to the ring nitrogen atom via its carbonyl carbon atom and to the ring carbon atom via its nitrogen atom, in which $R_3$ is selected from the group consisting of hydrogen and the R, Y, $Y_1$, $Y_2$ and $Y_3$ moieties defined below, R is selected from the group consisting of alkyl having up to 6 carbon atoms, optionally substituted by pyridyl or carbamoyl; alkenyl having up to 8 carbon atoms; aryl having up to 12 carbon atoms; and aralkyl having up to 12 carbon atoms; each said aryl group optionally being substituted by an —OH, —$NH_2$, —$NO_2$, alkyl having up to 8 carbon atoms, an alkoxy having up to 8 carbon atoms or by one or more halogens;

Y is selected from the group consisting of COR, COOH, COOR, CONHR, CONHOH, $CONHSO_2R$, $CH_2COOH$, $CH_2COOR$, $CH_2CONHOH$, $CH_2CONHCN$, $CH_2$tetrazole, $CH_2$(protected tetrazole), $CH_2SO_3H$, $CH_2SO_2R$, $CH_2PO(OR)_2$, $CH_2PO(OR)(OH)$, $CH_2PO(R)(OH)$ and $CH_2PO(OH)_2$, wherein R is as defined hereinabove;

$Y_1$ is selected from the group consisting of $SO_2R$, $SO_2NHCOR$, $SO_2NHCOOR$, $SO_2NHCONHR$ and $SO_3H$, wherein R is as defined hereinabove;

$Y_2$ is selected from the group consisting of $PO(OH)_2$, $PO(OR)_2$, PO(OH)(OR) and PO(OH)(R), wherein R is as defined hereinabove;

$Y_3$ is selected from the group consisting of tetrazole, tetrazole substituted by R, squarate, NRtetrazole, NRtetrazole substituted by R, and $NRSO_2R$, wherein R is as defined above.

The invention includes the pharmaceutically acceptable salts of these compounds, which can be obtained with inorganic or organic bases or acids.

The asymmetric carbon atom present in the compounds of formula (I) can exist in the R, S or RS configuration. The invention therefore also includes the compounds of formula (I) which exist in the form of pure enantiomers or in the form of a mixture of enantiomers, in particular, of racemates.

The term "alkyl having up to 8 carbon atoms" is understood to include, in particular, methyl, ethyl, propyl, isopropyl, linear or branched butyl, linear or branched pentyl and linear or branched hexyl.

The term "alkenyl having up to 8 carbon atoms" is understood to include, for example, allyl, butenyl, pentenyl and hexenyl.

The term "aryl having up to 12 carbon atoms" is understood to include phenyl and naphthyl.

The term "aralkyl having up to 12 carbon atoms" is understood to include benzyl, phenethyl and methylnaphthyl.

The term "alkoxy having up to 8 carbon atoms" is understood to include, in particular, methoxy, ethoxy, propoxy, isopropoxy, butoxy, isobutoxy, sec-butoxy and tert-butoxy.

The term "halo" or "halogen" is understood to include fluorine, chlorine, bromine and iodine.

The term "squarate" is understood to mean the radical of formula:

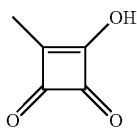

The term "heteroaryl" is understood to include, in particular, the following:

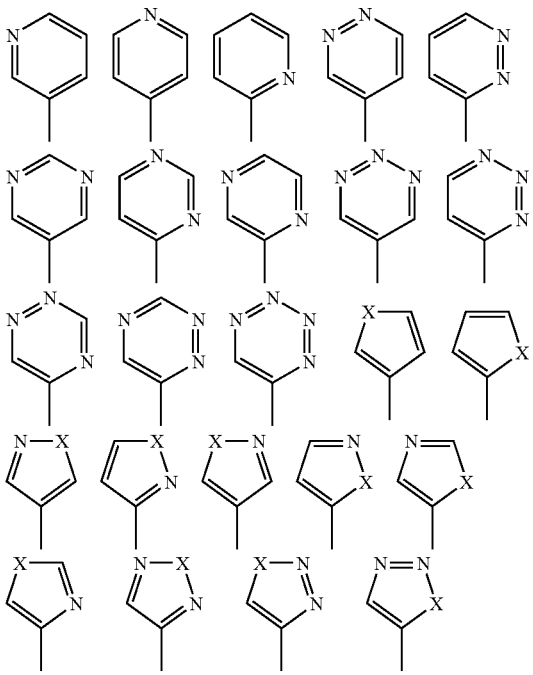

wherein X=S, O or $NR_4$ ($R_4$=H or alkyl).

The acid salts of the products of formula (I) include, inter alia, those formed with inorganic acids, such as hydrochloric acid, hydrobromic acid, hydroiodic acid, sulfuric acid and phosphoric acid, or with organic acids, such as formic acid, acetic acid, trifluoroacetic acid, propionic acid, benzoic acid, maleic acid, fumaric acid, succinic acid, tartaric acid, citric acid, oxalic acid, glyoxylic acid and aspartic acid, alkanesulfonic acids, such as methanesulfonic acid and ethanesulfonic acid, and arylsulfonic acids, such as benzenesulfonic acid and para-toluenesulfonic acid.

The base salts of the products of formula (I) include, inter alia, those formed with inorganic bases, such as, for example, sodium hydroxide, potassium hydroxide, lithium hydroxide, calcium hydroxide, magnesium hydroxide and ammonium hydroxide, or with organic bases, such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine, or, alternatively, phosphonium salts, such as alkylphosphoniums, arylphosphoniums, alkylarylphosphoniums and alkenylarylphosphoniums, or quaternary ammonium salts, such as tetra(n-butyl)ammonium salt.

Particularly preferred compounds of formula (I), are those in which n is equal to 1, those in which $R_2$ is hydrogen, those in which $R_1$ is selected from hydrogen, alkyl radical having up to 8 carbon atoms and $(CH_2)_{n'}R°_1$ in which n' is 0 or 1 and $R°_1$ is aryl, heteroaryl, CONR'R", CSNR'R", COCOOR', $SO_2NR'R"$, $SO_2R'$ or $CO_2R'$, the aryl radical having up to 12 carbon atoms, the heteroaryl radical having up to 15 carbon atoms and one or more heteroatoms selected from nitrogen, sulfur and oxygen, and R' and R" are as defined above, as well as those in which X is a divalent group —C(O)—N(OR_3)— in which $R_3$ is selected from the group consisting of hydrogen, R, Y and $Y_1$, R, Y and $Y_1$ being as defined above.

More particularly preferred compounds of formula (I), are the compounds selected from:

[[1,5-dihydro-1-(methylsulfonyl)-3-oxo-2,5-methano-2H-1,2,4-benzotriazepin-4(3H)-yl]oxy]acetic acid,

[[1-[(benzoylamino)carbonyl]-1,5-dihydro-3-oxo-2,5-methano-2H-1,2,4-benzotriazepin-4(3H)-yl]oxy]acetic acid,

[[1,5-dihydro-3-oxo-1-[(phenylsulfonyl)aminocarbonyl]-2,5-methano-2H-1,2,4-benzotriazepin-4(3H)-yl]oxy]acetic acid,

[(1,5-dihydro-3-oxo-2,5-methano-2H-1,2,4-benzotriazepin-4(3H)-yl)oxy]acetic acid, 4,5-dihydro-1-methyl-4-(sulfooxy)-2,5-methano-2H-1,2,4-benzotriazepin-3(1H)-one, 4,5-dihydro-4-(2-propenyloxy)-1-(3-pyridinylmethyl)-2,5-methano-2H-1,2,4-benzotriazepin-3(1H)one, 4,5-dihydro-3-oxo-N-(phenylsulfonyl)-4-(2-propenyloxy)-2,5-methano-2H-1,2,4-benzotriazepine-1(3H)-carboxamide, N-benzoyl-4,5-dihydro-3-oxo-4-(2-propenyloxy)-2,5-methano-2H-1,2,4-benzotriazepine-1(3H)-carboxamide, ethyl 4,5-dihydro-α,3-dioxo-4-(2-propenyloxy)-2,5-methano-2H-1,2,4-benzotriazepine-1(3H)-acetate, ethyl 4,5-dihydro-3-oxo-4-(sulfooxy)-2,5-methano-2H-1,2,4-benzotriazepine-1(3H)-acetate, and their salts as defined above.

The invention also includes a process for the preparation of the compounds of formula (I), this process comprising:

a) a first stage during which a compound of formula (II):

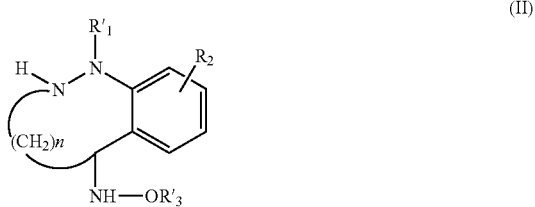

in which:

$R'_1$ is $R_1$ or a precursor thereof, $R_2$ and n are as defined in claim 1 and $R'_3$ is selected from the group consisting of a protective group for hydroxyl, Rp, Yp, $Y_1p$, $Y_2p$ and $Y_3p$, which, respectively, correspond to R, Y, $Y_1$, $Y_2$ and $Y_3$ as defined above, in which the possible reactive functional groups present are, if appropriate, protected, is reacted with a carbonylating agent, if appropriate in the presence of a base, for the purpose of obtaining an intermediate compound of formula (III):

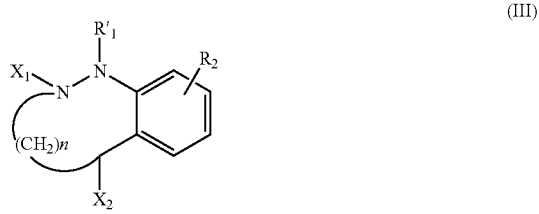

in which:

$R'_1$, $R_2$ and n are as defined above and either (1) $X_1$ is hydrogen and $X_2$ represents an —N(OR'$_3$)—CO—$X_3$ group, wherein $R'_3$ is as defined above and $X_3$ is the residue of the carbonylating agent, or (2) $X_2$ is —NH—OR'$_3$ and $X_1$ IS CO—$X_3$ group, $X_3$ being as defined above; and b) a second stage during which the intermediate of formula III obtained above is cyclized, in the presence of a base.

This process may further comprise, either before stage a) or after stage b), as appropriate:

c) one or more of the following reactions, in an appropriate order:
protection of the reactive functional groups,
deprotection of the reactive functional groups,
esterification,
saponification,
sulfonation,
phosphatation,
amidation,
acylation,
sulfonylation,
alkylation,
formation of a urea group,
introduction of a tetrazole group,
reduction of carboxylic acids,
dehydration of amide to nitrile,
salification,
exchange of ions,
separation of enantiomers,
nitration,
reduction of a nitro to an amino,
halogenation,
carbamoylation,
introduction of a cyano group.

Suitable carbonylating agents include phosgene, diphosgene, triphosgene, an aryl chloroformate, such as phenyl chloroformate or p-nitrophenyl chloroformate, an aralkyl chloroformate, such as benzyl chloroformate, an alkyl or alkenyl chloroformate, such as methyl chloroformate or allyl chloroformate, an alkyl dicarbonate, such as di(tert-butyl) carbonate, carbonyldimidazole and their mixtures.

The reaction preferably takes place in the presence of a base or of a mixture of bases that neutralizes the acid formed. The base can be, in particular, an amine, such as triethylamine, diisopropylethylamine, pyridine or dimethylaminopyridine. However, the reaction can also be carried out using the starting material of formula II as the base. An excess thereof is then used.

If appropriate, the product of formula II is employed in the form of an acid salt, for example a hydrochloride or a trifluoroacetate.

The base in stage b) may be selected from amines, alkali metal hydrides, alkoxides, amides or carbonates or alkaline earth metal hydrides, alkoxides, amides or carbonates.

The amines can be selected, for example, from the above list.

Sodium hydride or potassium hydride can, in particular, be used as the hydride.

Potassium t-butoxide is preferably used as the alkali metal alkoxide.

Lithium bis(trimethylsilyl)amide can, in particular, be used as the alkali metal amide.

Sodium carbonate, sodium bicarbonate, potassium carbonate or potassium bicarbonate can, in particular, be used as the carbonate.

If appropriate, the intermediate of formula III can be obtained in the form of an acid salt generated during the carbonylation reaction and, in particular, in the form of a hydrochloride. It is subsequently employed in the cyclization reaction in this form.

If appropriate, the cyclization can be carried out without isolation of the intermediate of formula III.

The reactions mentioned in stage c) are generally conventional reactions well known to a person skilled in the art. Illustrations are provided hereinafter in the experimental part.

The reactive functional groups that it is advisable, if appropriate, to protect are the carboxylic acid, amine, amide, hydroxyl and hydroxylamine functional groups.

The protection of the acid functional group is carried out, in particular, by forming alkyl esters, allyl esters or benzyl, benzhydryl or p-nitrobenzyl esters.

The deprotection is carried out by saponification, acid hydrolysis, hydrogenolysis or, alternatively, cleavage using soluble palladium(0) complexes.

The protection of the amines, heterocyclic nitrogens and amides is carried out, in particular, according to the circumstances, by forming benzyl or trityl derivatives, carbamates, in particular allyl, benzyl, phenyl or tert-butyl carbamates, or, alternatively, silyl derivatives, such as (tert-butyl)dimethylsilyl, trimethylsilyl, triphenylsilyl or diphenyl(tert-butyl)silyl derivatives, or phenylsulfonylalkyl or cyanoalkyl derivatives.

The deprotection is carried out, depending on the nature of the protective group, by sodium or lithium in liquid ammonia, by hydrogenolysis or using soluble palladium(0) complexes, by the action of an acid, or by the action of tetrabutylammonium fluoride or of strong bases, such as sodium hydride or potassium t-butoxide.

The protection of the hydroxylamines is carried out, in particular, by forming benzyl or allyl ethers.

The cleavage of the ethers is carried out by hydrogenolysis or by using soluble palladium(0) complexes.

The protection of the alcohols and phenols is carried out conventionally by forming ethers, esters or carbonates. The ethers can be alkyl or alkoxyalkyl ethers, preferably methyl or methoxyethoxymethyl ethers, aryl or, preferably, aralkyl ethers, for example, benzyl ethers, or silyl ethers, for example, the silyl derivatives mentioned above. The esters can be any cleavable ester known to a person skilled in the art, preferably, the acetate, the propionate or the benzoate or p-nitrobenzoate. The carbonates can be, for example, methyl, tert-butyl, allyl, benzyl or p-nitrobenzyl carbonates.

The deprotection is carried out by means known to a person skilled in the art, in particular, by saponification, hydrogenolysis, cleavage by soluble palladium(0) complexes, hydrolysis in an acidic medium or, alternatively, for silyl derivatives, treatment with tetrabutylammonium fluoride.

The sulfatation reaction is carried out by the action of $SO_3$-amine complexes, such as $SO_3$-pyridine or $SO_3$-dimethylformamide, the operation being carried out in pyridine, it being possible for the salt formed, for example, the pyridine salt, subsequently to be exchanged, for example, with a salt of another amine, of a quaternary ammonium or of an alkali metal.

The phosphatation reaction is carried out, for example, by the action of a chlorophosphate, such as dimethyl, dibenzyl or diphenyl chlorophosphate.

The amidation reaction is carried out starting from the carboxylic acid using an activating agent, such as an alkyl chloroformate, EDCI (1-(3-dimethylaminopropyl)-3-ethylcarbodiimide hydrochloride) or BOP (benzotriazol-1-yloxytripyrrolidinophosphonium hexafluorophosphate), by the action of ammonia or an appropriate amine or an acid salt thereof.

The acylation and sulfonylation reactions are carried out on the hydroxyureas, the alcohols, the amines or the heterocyclic nitrogens by the action, according to the circumstances, of an appropriate carboxylic acid or sulfonic acid halide or anhydride, if appropriate, in the presence of a base.

The alkylation reaction is carried out by the action, on the hydroxylated derivatives, the enolates of esters or of ketones, the amines or the heterocyclic nitrogens, according to the circumstances, of an alkyl sulfate or an alkyl or substituted alkyl halide, preferably, by a free or esterified carboxyl radical.

The reduction of acids to alcohols can be carried out by the action of a borane or, via an intermediate mixed anhydride, by the action of an alkaline borohydride. The mixed anhydride is prepared, for example, using an alkyl chloroformate. The reduction of aldehydes to alcohols is preferably carried out by the action of sodium borohydride.

The dehydration of amides to nitriles can take place under the conditions of the carbonylation and cyclization reactions.

The salification by acids is, if appropriate, carried out by addition of an acid in the soluble phase to the compound. The salification by bases can relate to the compounds comprising an acid functional group and, in particular, the compounds comprising a carboxyl functional group, those comprising a sulfoxy functional group or a functional group derived from phosphoric acid, or those comprising a heterocycle possessing an acidic nature.

In the case of a carboxyl functional group, the salification is carried out by addition of an appropriate base, such as those mentioned above. In the case of a sulfooxy functional group or functional group derived from phosphoric acid, the pyridinium salt is obtained directly during the action of the $SO_3$-pyridine complex and the other salts are obtained from this pyridinium salt. In either case, it is alternatively possible to operate by exchange of ions on a resin.

The nitration can be carried out by nitric acid or one of its metal salts in an acidic medium.

The reduction of a nitro group can be carried out by sodium dithionite or alternatively by zinc in acetic acid.

The term "halogenation" is understood to mean the introduction of a halogen substituent by the direct halogenation of the aromatic ring or by transformation of an aromatic hydroxy group to a halogen. According to the circumstances, the reaction can, for example, be carried out by the action of iodine or in the presence of triphenylphosphine, by the action of bromine in acetic acid or alternatively of iodine in the presence of $C_6H_5I(OCOCF_3)_2$, or, alternatively, by reaction of an electrophilic halogenated reagent, such as N-fluorosulfonylimide, in the presence of a strong base. Such reagents are known to a person skilled in the art.

The carbamoylation reaction can be carried out by the use of a chloroformate and then of an amine or, if appropriate, of ammonia.

The introduction of cyano is carried out by nucleophilic substitution using an alkaline cyanide or cyanogen bromide.

The separation of the enantiomers can be carried out according to techniques known to a person skilled in the art, in particular, by chromatography.

In addition to the processes described above, compounds of formula (I) can, of course, be obtained by methods that use, at the start, a compound of formula (II) in which $R'_1$, $R_2$ and $R'_3$ have the values which result directly (without conversion) in those of the compounds which it is desired to prepare. If appropriate, those of these values which would include reactive functional groups such as mentioned above are then protected, the deprotection taking place on conclusion of the cyclization stage b) or at any other opportune moment in the synthesis. The protection and deprotection are carried out as described above.

The invention also provides a process according to the above, but wherein the compound of formula (II) is obtained by a process according to which a compound of formula (IV):

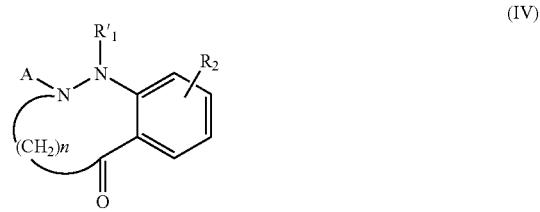

in which $R'_1$, $R_2$ and n are as defined above and A is hydrogen or a protective group for the nitrogen, is treated with a reducing agent, to obtain a compound of formula (V):

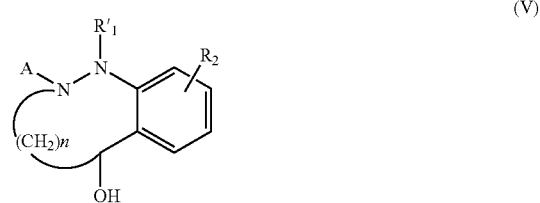

in which A, $R'_1$, $R_2$ and n are as defined above, and in which process, if appropriate, the OH group is replaced by a leaving group, to obtain a compound of formula (VI):

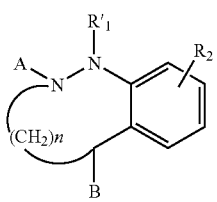

(VI)

in which A, R'$_1$, R$_2$ and n are as defined above mentioned meaning and B represents a leaving group, which compound of formula VI is then treated with a compound of formula NH$_2$—OR'$_3$, R'$_3$ being as defined above, and then, if appropriate, with an appropriate deprotecting agent for the nitrogen atom.

The invention further provides a process according to the above, but wherein the compound of formula (II) is obtained by a process according to which a compound of formula (IV) as defined above is treated with a compound of formula H$_2$N—OR'$_3$, to obtain a compound of formula (VII):

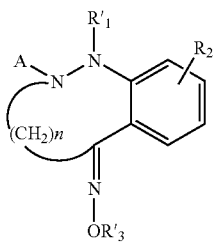

(VII)

in which A, R'$_1$, R$_2$, n and R'$_3$ are as defined above, which compound of formula VII is then reacted with a reducing agent, to obtain a compound of formula (VIII):

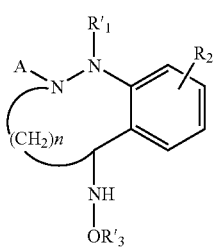

(VIII)

in which A, R'$_1$, R$_2$, n and R'$_3$ are as defined above, which compound of formula VIII is then treated, if appropriate, with an appropriate deprotecting agent for the nitrogen atom.

The protective group for the nitrogen is preferably one of those which are mentioned above.

The reducing agent is preferably an alkaline borohydride.

The leaving group is preferably a sulfonate, for example, a mesylate or a tosylate, obtained by the action of the corresponding sulfonyl chloride in the presence of a base, or a halide, more particularly, a chloride, a bromide or an iodide, obtained, for example, by the action of thionyl chloride or of P(C$_6$H$_5$)$_3$/CBr$_4$ or PBr$_3$ or, in the case of an iodide, by the action of an alkaline iodide on a sulfonate.

The deprotecting agent is preferably one of those mentioned above.

The reducing agent which acts on the compound of formula (VII) is preferably sodium cyanoborohydride or sodium acetoxyborohydride.

The compounds of general formula (I) have good antibiotic activity with regard to gram (+) bacteria, such as staphylococci. Their effectiveness with regard to gram (−) bacteria, in particular with regard to enterobacteria, is particularly significant.

These properties render said products, and their pharmaceutically acceptable acid and base salts, capable of being used as medicaments in the treatment of conditions involving sensitive microorganisms and in particular in that of staphylococcal infections, such as staphylococcal septicemia, malignant staphylococcal infections of the face or skin, pyodermatitis, septic or suppurating wounds, anthrax, abscesses, erysipelas, primary or post-influenza acute staphylococcal infections, bronchopneumonia or pulmonary suppurations.

These products can also be used as medicaments in the treatment of colibacillosis and associated infections, in proteus, klebsiella and salmonella infections and in other conditions brought about by gram (−) bacteria.

The compounds of general formula (I) furthermore possess inhibitory properties for β-lactamases and consequently are of advantage in combating infectious diseases or preventing the latter, in the form of a combination with various antibiotic compounds of β-lactam type, in order to strengthen their effectiveness in combating pathogenic bacteria producing β-lactamases.

It is well known that the enzymatic inactivation of antibiotics of β-lactam type, whether compounds of penicillin or cephalosporin type, in the treatment of bacterial infections, is an obstacle for compounds of this type. This inactivation consists of a process of decomposition of the β-lactams and constitutes one of the mechanisms by which bacteria can become resistant to treatments. It is therefore desirable to succeed in countering this enzymatic process by combining, with the antibacterial agent of β-lactam type, an agent capable of inhibiting the enzyme. When a β-lactamase inhibitor is used in combination with an antibiotic of β-lactam type, it can therefore strengthen its effectiveness against certain microorganisms.

Another subject matter of the present invention is therefore the use of compounds of formula (I) as defined above, and their salts with pharmaceutically acceptable acids and bases, and in particular the preferred compounds mentioned above, as medicaments and, in particular, medicaments intended for the treatment of bacterial infections in man or animals and medicaments intended to inhibit the production of β-lactamases by pathogenic bacteria.

Accordingly, the present invention provides a method of treating an infection or infection-causing condition in a mammal that is due to the presence of bacteria that generate beta-lactamases, which comprises administering to a mammal in need thereof an amount of a compound of claim 1 that is effective to inhibit beta-lactamase in said mammal.

The antibiotics of β-lactam type with which the compounds of formula (I) can be combined can be selected from the group consisting of penams, penems, carbapenems, cephems, carbacephems, oxacephems, cephamycins and monobactams.

The term "β-lactams" is understood to mean, for example, penicillins, such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin or pivampicillin, cephalosporins, such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditorenpivoxil, cefuroxime, cefuroxime axetil, loracarbacef or latamoxef, carbapenems, such as imipenem, meropenem, biapenem or panipenem, and monobactams, such as aztreonam and carumonam, and their salts.

The compounds of formula (I) or their pharmaceutically acceptable salts can be administered at the same time as antibiotics of β-lactam type are taken, or separately, preferably after antibiotics of β-lactam type have been taken. This can be carried out in the form of a mixture of the two active principles or in the form of a pharmaceutical combination of the two separate active principles.

The dosage of the compounds of formula (I) and of their pharmaceutically acceptable salts can, of course, vary within wide limits and should naturally be adapted, in each specific case, to the individual conditions and to the pathogenic agent to be combated. Generally, for use in the treatment of bacterial infections, the daily dose can be between 0.250 g and 10 g per day, orally in man, with the product described in Example 11, or between 0.25 g and 10 g per day, intramuscularly or intravenously. For use as β-lactamase inhibitor, a daily dose in man which can range from 0.1 to approximately 10 g may be suitable.

Furthermore, the ratio of the β-lactamase inhibitor of formula (I) or of the pharmaceutically acceptable salt of the latter to the antibiotic of β-lactam type can also vary within wide limits and should be adapted, in each specific case, to the individual conditions. Generally, a ratio ranging from approximately 1:20 to approximately 1:1 should be employed.

The antibiotic medicaments or β-lactamase inhibitor medicaments as defined above are employed in the form of pharmaceutical compositions as a mixture with an organic or inorganic, inert pharmaceutical excipient adapted to the desired method of administration, and the present invention also includes pharmaceutical compositions comprising, as active principle, at least one of the compounds of the invention as defined above.

These compositions can be administered buccally, rectally, parenterally, in particular, intramuscularly, or locally by topical application to the skin and mucous membranes.

These compositions can be solid or liquid and are provided in the pharmaceutical forms commonly used in human medicine, such as, for example, simple or sugar-coated tablets, hard gelatin capsules, granules, suppositories, injectable preparations, ointments, creams or gels; they are prepared according to conventional methods. The active principle or principles can be incorporated therein with excipients commonly employed in such pharmaceutical compositions, such as talc, gum arabic, lactose, starch, magnesium stearate, cocoa butter, aqueous or nonaqueous vehicles, fatty substances of animal or vegetable origin, paraffin derivatives, glycols, various wetting, dispersing or emulsifying agents, and preservatives.

These compositions can also be provided in the form of a lyophilisate that is intended to be dissolved at the time of use in an appropriate vehicle, for example sterile apyrogenic water.

The products of formula (I) can also be used as disinfecting agents for surgical instruments.

The invention also provides, as novel intermediate compounds:
the products of formula (III) as defined above and their salts with acids and, in particular, their hydrochlorides and trifluoroacetates,
the products of formula (II) as defined above and their salts with acids and, in particular, their hydrochlorides and trifluoroacetates,
and the products of formulae (IV), (V), (VI), (VII) and (VIII) as defined above and their salts with an acid and, in particular, their hydrochlorides and trifluoroacetates.

These novel industrial products are intermediates especially useful for the preparation of the products of formula (I).

The products of formula (IV) can be prepared, for example, according to methods provided hereinafter in the experimental part.

The following examples illustrate the invention without, however, limiting the scope thereof.

EXAMPLE 1

4-(2-Propenyloxy)-2,3,4,5-tetrahydro-2,5-methano-1H-1,2,4-benzotriazepin-3-one

Stage A: 4-Cinnolinol hydrochloride 560 ml of concentrated hydrochloric acid are introduced into a reactor. 111.6 g of 2-acetylaniline are added at ambient temperature. 62.8 g of sodium nitrite, in solution in 170 ml of water, are added to this orange-colored solution at −5° C. over 1 hour. The temperature is kept below 0° C. throughout the introduction. The reaction medium is heated at 65° C. for 3 hours. The mixture is subsequently cooled over 20 minutes and the product is then filtered off and washed with ether. The compound is dried over $P_2O_5$ at 45° C. overnight. 118.6 grams (77%) of the expected product are obtained.

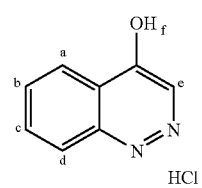

NMR spectrum: ($d_6$-DMSO) 1H: 7.43 ppm (bt, J=7.5) 1H: 7.80 ppm (td, J=7.5 and 1.5) Hb and Hc; 1H: 7.68 ppm (bd, J=7.5). 1H: 8.04 ppm (bd, J=7.5) Ha and Hd; 1H: 7.76 ppm (s) He; 1H: 13.8 ppm (s) OH. Mass spectrum: 146+M+. 36+/38+ Characteristic doublet $H^{35}Cl^+/H^{37}Cl^+$. IR spectrum: 1625/1564 cm$^{-1}$ aromatic+conjugated system. UV spectrum: 242 nm $\epsilon$=8700; 340 nm $\epsilon$=6700.

Stage B: 2,3-Dihydro-4(1H)-cinnolinone hydrochloride 69.41 g of the product obtained in stage A are dissolved in 2.5 l of ethanol. 62.79 g of zinc powder are subsequently added, followed, slowly, by a mixture of 300 ml of ethanol and 150 ml of acetic acid at ambient temperature. The mixture is heated at reflux for 30 min. The reaction medium is subsequently separated by settling, and the zinc residue is washed several times with ethanol. After being allowed to cool for 20 minutes in an ice/methanol mixture (−15° C.), a solution of hydrogen chloride gas in ethyl acetate is then added (350 ml; 4M). The precipitate formed is filtered off, washed with ether and then with pentane, and finally dried (under reduced pressure). 42.12 grams (60%) of the expected product are obtained.

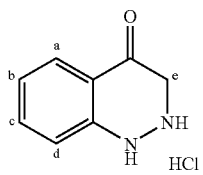

NMR spectrum: (d$_6$-DMSO) 2H: 4.04 ppm (s) He; 1H: 7.00 ppm (td, J=8 and 1.5) 1H: 7.55 ppm (td, J=8 and 1.5) Hb and Hc; 1H: 7.06 ppm (bd, J=8) 1H: 7.73 ppm (dd, J=8 and 1.5) Ha and Hd; 1H: 9.77 ppm (s) mobile proton. Mass spectrum: 148+M+; 119+M+; 92+M+; 36+/38+ salification of the product. IR spectrum: 1686 cm$^{-1}$ ν(C=O); 1606, 1550, 1520 cm$^{-1}$ aromatic+conjugated system.

Stage C: 1,1-Dimethylethyl 3,4-dihydro-4-oxo-2(1H)-cinnoline carboxylate 82.16 g of the product obtained in stage B are dissolved in THF (1.7 l). 106.72 g of di(t-butyl) dicarbonate are subsequently added, followed, dropwise over 15 min, by 94.4 g of triethylamine. The mixture is left stirring for 20 hours and is then filtered to remove the triethylamine salts, which are rinsed with THF. The solvent is evaporated and the residue is taken up in a heptane/AcOEt (1:2) mixture and NaH$_2$PO$_4$ (1M aqueous solution). Extraction is carried out with ethyl acetate and washing is carried out with water. The organic phase is dried over MgSO$_4$ and then evaporated to dryness. 65.42 grams (59%) of the expected product are obtained.

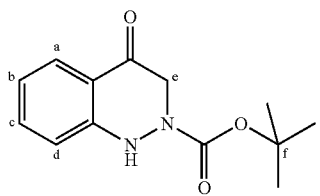

NMR spectrum: (CDCl$_3$) 9H: 1.46 ppm (s) Hf; 2H: 4.38 ppm (s) He; 1H: 6.91 ppm (bd, J=8) Hd or Ha; 1H: 6.96 ppm (td, J=8 and 1.5) Hc; 1H: 7.43 ppm (td, J=8 and 1.5) Hb; 1H: 7.91 ppm (dd, J=8 and 1.5) Ha or Hd; 1H: 7.1 ppm (s) mobile proton. Mass spectrum: 248+M+; 233+M+-CH$_3$; 192+M+-tBu; 148+M+-boc; 119+M+-[-(NH—Nboc)—]; 57+tBu+; IR spectrum: 1712, 1670 cm$^{-1}$ ν(C=O); 1610, 1578 cm$^{-1}$ ν(C=C) aromatic.

Stage D: 1,1-Dimethylethyl 3,4-dihydro-4-[(2-propenyloxy) imino]-2(1H)-cinnoline carboxylate 30.8 g of the product obtained in stage C are dissolved in 200 ml of pyridine. 14.95 g of alkylhydroxylamine are added with stirring under argon. After one hour, the pyridine is evaporated. The residue is taken up in a heptane/AcOEt (1:2) mixture and NaHSO$_4$ (10% aqueous solution). Extraction is carried out with ethyl acetate and washing is carried out with water. The organic phase is dried over MgSO$_4$ and evaporated to dryness. 36.08 g of the expected product (96%) are isolated.

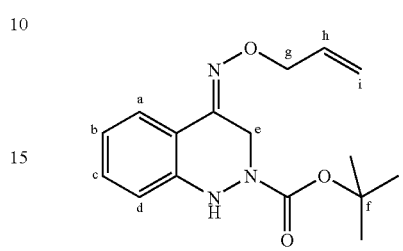

NMR spectrum: (CDCl$_3$) 9H: 1.44 ppm (s) Hf; 2H: 4.73 ppm (s) He; 2H: 4.69 ppm (td, J=5.5 and 1) Hg; 1H: 5.22 ppm (dq, J=10 and 1); Hi1; 1H: 5.32 ppm (dq, J=17.5 and 1) Hi2; 1H: 6.05 ppm (m) Hh; 1H: 6.91 ppm (td, J=8 and 1.5); 1H: 7.22 ppm (td, J=8 and 1.5) Hb and Hc; 1H: 6.81 ppm (bd, J=8) 1H: 7.86 ppm (dd, J=8 and 1.5) Ha and Hd. Mass spectrum: 304+MH+; 247+M+-(O—CH$_2$—CH=CH$_2$). IR spectrum: 1708 cm$^{-1}$ ν(C=O); 1638, 1610, 1589, 1494 cm$^{-1}$ aromatic+conjugated system.

Stage E: 1,1-Dimethylethyl 3,4-dihydro-4-[(2-propenyloxy) amino]-2(1H)-cinnoline carboxylate 19 g of the product obtained in stage D are dissolved in 2 l of methanol and then 63.18 g of sodium cyanoborohydride are added. 107.03 g (95.5 ml) of boron trifluoride etherate are introduced dropwise at 0° C. After evaporating the methanol, the residue is treated with NaH$_2$PO$_4$ (1M aqueous solution) and then extraction is carried out with a heptane/AcOEt (1:2) mixture. Washing is subsequently carried out with water, and the organic phase is dried with MgSO$_4$ and evaporated to dryness. The compound is taken up in an ether/pentane mixture at 0° C. The compound crystallizes. 13.95 g of the expected product (73%) are isolated.

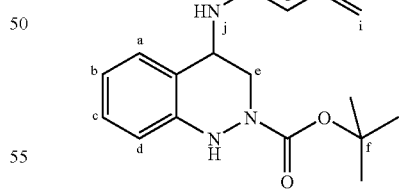

NMR spectrum: (CDCl$_3$): 9H: 1.49 ppm (s) Hf; 1H: 3.35 ppm (d) He1; 1H: 4.60 ppm (dd) He2; 1H: 4.15 ppm (t) Hj; 1H: 4.30 ppm (m) Hg; 1H: 5.20 ppm (m) Hi1; 1H: 5.30 ppm (m) Hi2; 1H: 5.96 ppm (m) Hb; 1H: 6.75 ppm Hh; 1H: 6.86 ppm Hd; 1H: 7.16 ppm Hc; 1H: 7.28 ppm Ha. Mass spectrum: 305+M+; 205+M+-CO$_2$tBu+H; 57+tBu+. IR spectrum: 3344 cm$^{-1}$ ν(NH); 1708 cm$^{-1}$ ν(C=O); 1638, 1610, 1589, 1494 cm$^{-1}$ ν(C=C)+aromatic. UV spectrum: 244 nm ε=8500; 290 nm ε=2000. Microanalysis:

| Calculated: | Obtained: |
|---|---|
| % C: 62.9% | % C: 63% |
| % H: 7.5% | % H: 7.6% |
| % N: 13.8% | % N: 13.7% |

Stage F: 1,2,3,4-Tetrahydro-4-[(2-propenyloxy)amino]cinnoline dihydrochloride 11.28 g of the product obtained in stage E are dissolved in 43 ml of ethyl acetate and then 70 ml of a 5.3M solution of hydrogen chloride gas in ethyl acetate are added at 0° C., with stirring and under argon. After 30 min, the precipitate is filtered off, washed with ether and then dried. 8.93 g of the expected compound (100%) are isolated.

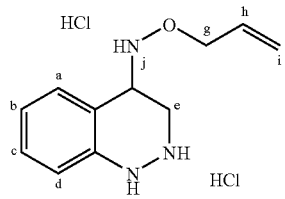

NMR spectrum: ($d_6$-DMSO): 1H: 3.37 ppm (dd, J=4 and 13) $He_1$; 1H: 3.68 ppm (dd, J=3 and 13) $He_2$; 2H: 4,23 ppm (td, J=5.5 and 1) Hg; 1H: 4,28 (dd, J=3 and 4) Hj; 1H: 5.18 ppm (dq, J=10.5 and 1.5) Hi1; 1H: 5.29 ppm (dq, J=17.5 and 1.5) Hi2; 1H: 5.95 ppm (m) Hh; 1H: 6.83 ppm (dd, J=7.5 and 1), 1H: 7.39 ppm (dd, J=7.5 and 1) Ha and Hd; 1H: 6.93 (td, J=7.5 and 1); 1H: 7.21 ppm (td, J=7.5 and 1) Hb and Hc; 1H: 7.32 (bs) mobile proton; 1H: 8,96 (bs) mobile proton; 1H: 11.00 (bs) mobile proton; 1H: 11.78 (bs) mobile proton. Mass spectrum: 205+M+; 36+/38+$H^{35}$Cl+/$H^{37}$Cl+. IR spectrum: >3000 $cm^{-1}$ ν(NH); 1642 $cm^{-1}$ ν(C=C); 1612, 1590, 1530, 1497 $cm^{-1}$ ν(C=C)+aromatic; Microanalysis:

| Calculated (with two hydrochlorides): | Obtained: |
|---|---|
| % C: 47.5% | % C: 47.8% |
| % H: 6.2% | % H: 6.1% |
| % N: 15.1% | % N: 15.2% |
| % Cl: 25.5% | % Cl: 24.7% |

Stage G: 4,5-Dihydro-4-(2-propenyloxy)-2,5-methano-2H-1,2,4-benzotriazepin-3(1H)-one 8.93 g of the product obtained in stage F are dissolved in 3.7 l of acetonitrile. 14.92 g (20.6 ml) of triethylamine are added dropwise. 3.66 g (2.25 ml) of diphosgene are subsequently introduced over 5 min at 0° C., followed by 4.96 g of dimethylaminopyridine. The mixture is subsequently allowed to return to ambient temperature. After one hour, the acetonitrile is evaporated and the residue is treated with $NaH_2PO_4$ (1M aqueous solution). Extraction is carried out with a heptane/AcOEt (1:2) mixture and washing is carried out with water. The organic phase is dried over $MgSO_4$. It is filtered and evaporated and the compound is taken up in ether at 0° C. It crystallizes. 3.94 g of the expected compound (46%) are obtained.

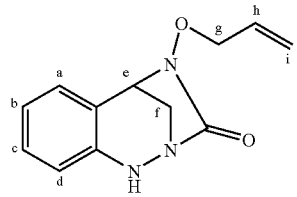

NMR spectrum: ($CDCl_3$): 1H: 3.29 ppm (d, J=11.5) Hfl, 1H: 3.70 ppm (dd, J=11.5 and 3) Hf2; 1H: 4.38 ppm (d, J=3) He; 2H: 4.42 ppm (bd, J=6) Hg; 1H: 6.02 ppm (m) Hh; 1H: 5.33 ppm (bd, J=10.5) Hi1; 1H: 5.38 ppm (bd, J=17) Hi2; 1H: 6.63 ppm (dd, J=8 and 1); 1H: 7.10 ppm (dd, J=8 and 1.5) Ha and Hd; 1H: 6.82 ppm (td, J=8 and 1), 1H: 7.21 ppm (td, J=8 and 1.5) Hc and Hb. Mass spectrum: 231+M+; 174+M+-(O—$CH_2$—CH=$CH_2$); 131+opening of the carbamate ring. IR spectrum: 3312 $cm^{-1}$ ν(NH); 1744 $cm^{-1}$ ν(C=O); 1648 ν(C=C); 1608, 1582, 1492 $cm^{-1}$ aromatic. UV spectrum: 246 nm ε=7400; 291 nm ε=1800. Microanalysis:

| Calculated: | Obtained: |
|---|---|
| % C: 62.3% | % C: 62.1% |
| % H: 5.7% | % H: 5.5% |
| % N: 18.2% | % N: 18.1% |

EXAMPLE 2

4-Benzyloxy-2,3,4,5-tetrahydro-2,5-methano-1H-1,2,4-benzotriazepin-3-one

Stage A: 1,1-Dimethylethyl 3,4-dihydro-4-(phenylmethoxy)imino-2(1H)-cinnoline carboxylate 3 g of the compound obtained in stage C of Example 1 are dissolved in 25 ml of pyridine and then 2.12 g of benzylhydroxylamine hydrochloride are added with stirring and under argon. After one hour, the pyridine is evaporated. The residue is taken up in a heptane/AcOEt 1:2 mixture and $NaHSO_4$ (10% solution in $H_2O$). Extraction is carried out with ethyl acetate and washing is carried out with water. The organic phase is dried over $MgSO_4$. It is filtered, the solvent is evaporated and 4.3 g of the expected compound (100%) are isolated.

Stage B: 1,1-Dimethylethyl 3,4-dihydro-4-[(phenylmethoxy)amino]-2(1H)-cinnoline carboxylate 4.27 g of the compound obtained in stage A are dissolved in 450 ml of methanol. 12.14 g of sodium cyanoborohydride are subsequently added, followed, dropwise at 0° C., by 20.57 g (18.36 ml) of boron trifluoride etherate. After evaporating the methanol, the residue is treated with $NaH_2PO_4$ (1M aqueous solution) and then extraction is carried out with a heptane/AcOEt 1:2 mixture. Washing is subsequently carried out with an acidic aqueous solution and then the organic phase is dried with $MgSO_4$ and the solvent is evaporated. The compound is taken up in an ether/pentane mixture at 0° C. The compound crystallizes. 3.81 g of the expected compound (89%) are isolated.

17

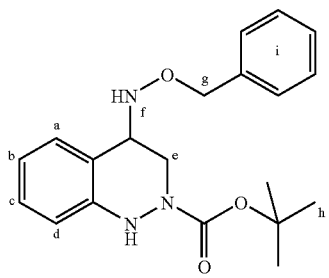

NMR spectrum: (CDCl$_3$) 9H: 1.51 ppm (s) Hh; 1H: 3.35 ppm (bd, J=13.5) He1; 1H: 4.63 ppm (bd, J=13.5) He2; 1H: 4.10 ppm (t, J=2) Hf; 2H: 4.81 ppm system of AB type Hg; 1H: 6.75 ppm (d, J=8), 1H: 6.83 ppm (td, J=8 and 1.5), 2H: 7.16 ppm (m): Ha, b, c, d; 5H: 7.26 to 7.42 ppm Hi. Mass spectrum: 356+MH+; 378+MNa+; 733+[2M+Na]+; 300+MH+-tBu; 233+MH+-(—NH—O—CH$_2$-Ph); 177+233+-tBu; 133+233+-CO$_2$tBu; 106+(Ph—CH$_2$—O)+.

Stage C: 1,2,3,4-Tetrahydro-4-[(phenylmethoxy)amino]-cinnoline dihydrochloride 3.81 g of the compound obtained in stage B are dissolved in 15 ml of ethyl acetate, and then 25 ml of a 4.3M solution of hydrogen chloride gas in ethyl acetate are added at 0° C. with stirring and under argon. After 30 min, the reaction medium is filtered and the filter residue is washed with ether. The compound is dried and 3.13 g of the expected compound (89%) are isolated.

Stage D: 4,5-Dihydro-4-(phenylmethoxy)-2,5-methano-2H-1,2,4-benzotriazepin-3(1H)-one 3.13 g of the compound obtained in stage C are dissolved in 1.9 l of acetonitrile. 4.81 g (6.6 ml) of triethylamine are added dropwise over 10 minutes. 0.943 g (575 µl) of diphosgene is subsequently added slowly at 0° C., followed by 1.27 g of dimethylaminopyridine. The temperature is subsequently allowed to return to ambient temperature. After one hour, the acetonitrile is evaporated and the residue is treated with NaH$_2$PO$_4$ (1M aqueous solution). Extraction is carried out with a heptane/AcOEt 1:2 mixture and washing is carried out with water. The organic phase is dried over MgSO$_4$ and evaporated to dryness. This residue is crystallized from ether at 0° C. 1.82 g of the expected compound (68%) are obtained.

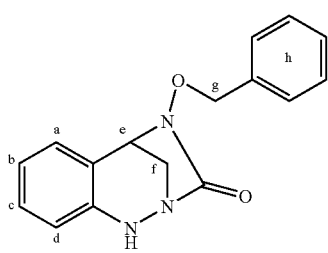

NMR spectrum: (CDCl$_3$): 1H: 3.16 ppm (d, J=11) Hf1, 1H: 3.55 ppm (dd, J=11 and 2.5) Hf2; 1H: 3.80 ppm (d, J=2.5) He; 1H: 4.86 ppm, 1H: 4.98 ppm system of AB type Hg; 1H: 6.60 ppm (bd, J=8), 1H: 6.93 ppm (dd, J=8 and 1.5) Ha and Hd; 1H: 6.80 ppm (td, J=8 and 1.5), 1H: 7.19 ppm (td, J=8 and 1.5) Hb and Hc; 5H: 7.43 ppm (m) Hh. Mass spectrum: 281+M+; 174+M+-(O—CH$_2$-Ph); 131+ opening of the carbamate ring; 91+PhCH$_2$+. IR spectrum: 3320 cm$^{-1}$ ν(NH); 1746 cm$^{-1}$ ν(C=O); 1607, 1580, 1490 cm$^{-1}$ aromatic. UV spectrum: 247 nm ε=7000; 290 nm ε=1800. Microanalysis:

| Calculated: | Obtained: |
| --- | --- |
| % C: 68.3% | % C: 67.7% |
| % H: 5.4% | % H: 5.4% |
| % N: 14.9% | % N: 14.7% |

EXAMPLE 3

2-Propenyl [(3-oxo-2,3,4,5-tetrahydro-2,5-methano-1H-1,2,4-benzotriazepin-4-yl)oxy]acetate Stage A: 1,1-Dimethylethyl 4-[(carboxymethoxy)imino]-3,4-dihydro-2(1H)-cinnoline carboxylate 3 g of the compound obtained in stage C of example 1 are dissolved in 25 ml of pyridine, and then 3.9 g of carboxymethylhydroxylamine are added with stirring and under argon. After one hour, the pyridine is evaporated and the residue is taken up in a heptane/AcOEt (1:2) mixture and NaHSO$_4$ (10% aqueous solution). Extraction is carried out once with ethyl acetate, and washing is carried out with water. The organic phase is subsequently dried over MgSO$_4$. It is filtered, the solvent is evaporated and 3.56 g of the expected compound (92%) are isolated.

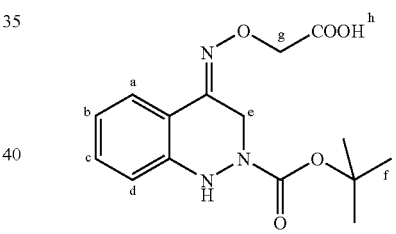

NMR spectrum: (d$_6$-DMSO): 9H: 1.35 ppm (s)Hf; 2H: 4.63 ppm (s), 2H: 4.67 ppm (s) He and Hg; 1H: 6.81 ppm (td, J=8 and 1.5), 1H: 7.24 ppm (td, J=8 and 1.5) Hb and Hc; 1H: 6.96 ppm (bd, J=8), 1H: 7.62 ppm (bd, J=8) Ha and Hd; 1H: 8.49 ppm (bs) NH; 1H: 12.82 ppm (s) Hh. Mass spectrum: 322+MH+; 344+MNa+; 643+(2M+H)+; 266+MH+-tBu; 146+MH+-boc—(O—CH$_2$—COOH). IR spectrum: 3344 cm$^{-1}$ ν(NH); 1708 cm$^{-1}$ ν(C=O); 1638, 1610, 1589, 1494 cm$^{-1}$ ν(C=C)+aromatic. UV spectrum: 236 nm ε=14800; 259 nm ε=12600; 330 nm ε=4000. Microanalysis:

| Calculated: | Obtained: |
| --- | --- |
| % C: 56.1% | % C: 55.7% |
| % H: 6% | % H: 5.8% |
| % N: 13.1% | % N: 13.3% |

Stage B: 1,1-Dimethylethyl 3,4-dihydro-4-[[2-oxo-2-(2-propenyloxy)ethoxy]imino]-2(1H)-cinnoline carboxylate 15.5 g of the product obtained as described in stage A are dissolved in 200 ml of DMF. 12.17 g of sodium bicarbonate and 17.53 g (12.5 ml) of allyl bromide are added to the solution. After 48 hours at ambient temperature with stirring under argon, the reaction medium is treated with a heptane/AcOEt (1:2) mixture and NaH$_2$PO$_4$ (1M aqueous solution). After extracting with heptane/AcOEt (1:2) and washing the organic phase with water and then with a saturated aqueous sodium bicarbonate solution, the organic phase is dried over MgSO$_4$ and the solvent is evaporated. The product is crystallized from pentane. 12.68 g of the expected product (81%) are isolated.

followed, at 0° C., by 1.658 g of diphosgene and 2.25 g of dimethylaminopyridine. The temperature is allowed to return to ambient temperature. After one hour, the acetonitrile is evaporated and the residue is treated with NaH$_2$PO$_4$ (1M aqueous solution). Extraction is carried out with AcOEt, and the organic phase is washed with water. It is dried over MgSO$_4$ and the solvent is evaporated. The residue is chromatographed on silica (eluent: heptane/AcOEt (4:1)). The compound obtained is crystallized from ether at 0° C. and 1.96 g of the expected product (41%) are isolated.

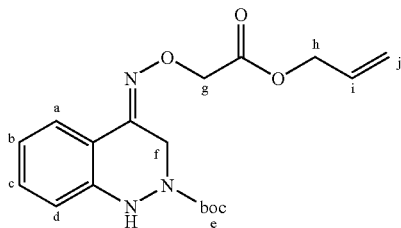

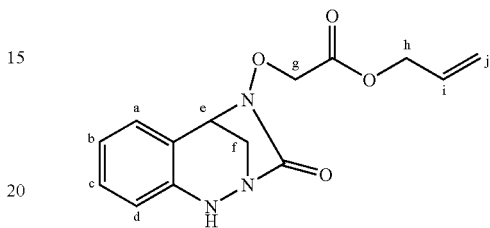

NMR spectrum: (CDCl$_3$) 9H: 1.45 ppm (s) He; 2H: 4.69 ppm (d) Hh; 1H: 5.93 ppm (m) Hi; 1H: 5.25 ppm (qd) Hj1; 1H: 5.35 ppm (qd) Hj2; 2H: 4.76 ppm (s) Hg; 2H: 4.80 ppm (s) Hf; 1H: 6.81 ppm (d) Hd; 1H: 6.89 ppm (td) Ha; 1H: 7.23 ppm (td) Hb; 1H: 7.81 ppm (dd) Hc. Mass spectrum: 362+MH+; 384+MNa+; 328+MNa+-tBu; 369+MNa+-tBu+CH$_3$CN; Presence of diallyl structure: 424+MNa+; 402+MH+; 346+MH+-tBu. IR spectrum: 3475 cm$^{-1}$ ν(NH); 3365, 3340 cm$^{-1}$ ν(C=O); 1757, 1698 cm$^{-1}$ ν(C=C); 1645 cm$^{-1}$ aromatic; 1622, 1608, 1578 cm$^{-1}$. UV spectrum: 237 nm ε=14500; 259 nm ε=12000; 330 nm ε=3800.

Stage C: 1,1-Dimethylethyl 3,4-dihydro-4-[[2-oxo-2-(2-propenyloxy)ethoxy]amino]-2(1H)-cinnoline carboxylate 12.68 g of the product obtained in stage B are dissolved in 1.4 l of methanol. 35.3 g of sodium cyanoborohydride are added at 0° C., followed, dropwise, by 59.75 g of boron trifluoride etherate. After evaporating the methanol, the residue is treated with NaH$_2$PO$_4$ (1M aqueous solution) and then extraction is carried out with a heptane/AcOEt (1:2) mixture. The organic phase is washed with water and dried with MgSO$_4$, and the solvent is evaporated. The compound is subsequently passed through silica (eluent: heptane/t-BuOMe (4:1)). 6.16 g of the expected product (48%) are isolated.

Stage D: 2-Propenyl [[(1,2,3,4-tetrahydro-4-cinnolinyl)amino]oxy]acetate dihydrochloride The 6.16 g of the product obtained in stage C are dissolved in 22 ml of ethyl acetate, and then 38 ml of a 4.3M solution of hydrogen chloride gas in ethyl acetate are added at 0° C. with stirring and under argon. The mixture is brought back to ambient temperature. After 30 min, the precipitate is filtered off, washed with ether and dried under reduced pressure. 5.63 g of the expected product (99%) are isolated.

Stage E: 2-Propenyl [(1,5-dihydro-3-oxo-2,5-methano-2H-1,2,4-benzotriazepin-4(3H)-yl)oxy]acetate 5.63 g of the product obtained in stage D are dissolved in 2 l of acetonitrile. 8.45 g of triethylamine are slowly added, NMR spectrum: (CDCl$_3$) 1H: 3.32 ppm (d) Hf1; 1H: 3.69 ppm (dd) Hf2; 1H: 4.83 ppm (d) He; 2H: 4.55 ppm (s) Hg; 2H: 4.71 ppm (d) Hh; 1H: 5.96 ppm (m) Hi; 1H: 5.32 ppm (qd) Hj1; 1H: 5.38 ppm (qd) Hj2; 1H: 6.64 ppm (d) Hd; 1H: 7.28 ppm (dd) Ha; 1H: 6.85 ppm (td) Hb; 1H: 7.22 ppm (td) Hc. Mass spectrum: 290+MH+; 312+(M+Na)+; 601+(2M+Na)+; IR spectrum: 3320 cm$^{-1}$ ν(NH); 1746 cm$^{-1}$ ν(C=O); 1678, 1580, 1490 cm$^{-1}$ aromatic.

EXAMPLE 4

2-Propenyl [[1,5-dihydro-1-(methylsulfonyl)-3-oxo-2,5-methano-2H-1,2,4-benzotriazepin-4(3H)-yl]oxy]acetate 100 mg of the product obtained in example 3 are dissolved in 2 ml of anhydrous CH$_2$Cl$_2$. 43.53 mg of methanesulfonic chloride are subsequently added at 0° C., followed by 38.4 mg of triethylamine and then 46.4 mg of dimethylaminopyridine. After 10 minutes, the solvent is evaporated. The residue is treated with a heptane/AcOEt (1:2) mixture and NaH$_2$PO$_4$ (1M aqueous solution). After extracting with AcOEt, then washing the organic phase with water and drying over MgSO$_4$, the solvent is evaporated. 114.5 mg of the expected product (90%) are isolated.

EXAMPLE 5

N-(1-Methylethyl)-2-propanaminium salt of [[1,5-dihydro-1-(methylsulfonyl)-3-oxo-2,5-methano-2H-1,2,4-benzotriazepin-4(3H)-yl]oxy]acetic acid 112 mg of the product obtained in example 4 are dissolved in 0.8 ml of THF. 35.3 mg of tetrakis (triphenylphosphine) palladium and then 154.2 mg of diisopropylamine are added to the solution. The reaction mixture is left at 0° C. with stirring and under argon for 20 minutes. 0.1 ml of ether is added and then the solid is filtered off and washed with 1 ml of a THF/ether (4:1) mixture. 99.5 mg of the expected product (76%) are isolated.

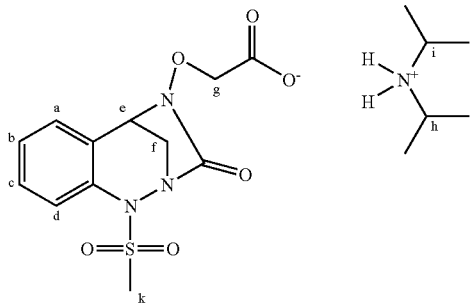

NMR spectrum: (d$_6$-DMSO) 12H: 1.19 ppm (d, J=6.5) Hh; 2H: 3.27 ppm (sept, J=6.5) Hi; 1H: 3.44 ppm (d, J=9) Hf1; 1H: 3.65 ppm (dd, J=2.5) Hf2; 1H: 5.22 ppm (d, J=2.5) He; 3H: 3.39 ppm (s) Hk; 1H: 7.45 ppm (dd, J=8 and 1.5) Ha; 1H: 7.10 ppm (td, J=8 and 1.5) Hb; 1H: 7.35 ppm (td, J=8 and 1.5) Hc; 1H: 7.61 ppm (dd, J=8 and 1.5) Hd. Mass spectrum: 102+M+; 279+Ph$_3$P=O+; 326– M–. UV spectrum: 278 nm ϵ=1400; 322 nm ϵ=1200; inflection at 260, 275, 286 nm.

EXAMPLE 6

2-Propenyl [[1-[(benzoylamino)carbonyl]-1,5-dihydro-3-oxo-2,5-methano-2H-1,2,4-benzotriazepin-4(3H)-yl]oxy]acetate 100 mg of the product obtained in example 3 are dissolved in 5 ml of toluene. 50.85 mg of benzoyl isocyanate are added at 0° C. The mixture is allowed to return to ambient temperature. After stirring for one hour under argon, the product is filtered off and washed with 1 ml of toluene. It is dried, and 80 mg of the expected product (53%) are isolated.

EXAMPLE 7

N-(1-Methylethyl)-2-propanaminium salt of [[1-[(benzoylamino)carbonyl]-1,5-dihydro-3-oxo-2,5-methano-2H-1,2,4-benzotriazepin-4(3H)-yl]oxy] acetic acid 80 mg of the product obtained in example 6 are dissolved in 0.8 ml of THF. 21.2 mg of tetrakis(triphenylphosphine) palladium and then 92.6 mg of diisopropylamine are added to the solution. The reaction mixture is left at 0° C. with stirring and under argon for 20 minutes. 0.1 ml of ether is added and then the product is filtered off. The solid is washed with 1 ml of a THF/ether (4:1) mixture. 50.9 mg of the expected product (56%) are isolated.

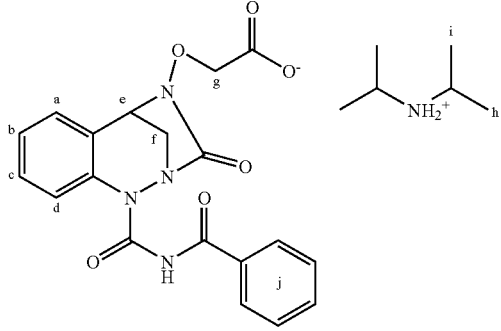

NMR spectrum: (d$_6$-DMSO): 12H: 1.18 ppm (d, J=6.5) Hh; 2H: 3.26 ppm (sept, J=6.5) Hi; 1H: 3.55 ppm (d, J=11.5) Hf1; 1H: 3.78 ppm (dd, J=11.5 and 2.5) Hf2; 1H: 5.30 ppm (d, J=2.5) He; 2H: 4.07 ppm system of AB type Hg; 9H: 7.12-8.35 ppm (m); Ha, Hb, Hc, Hd, Hj; <1H: 8.84 ppm (bs) mobile H. Mass spectrum: 397+MH+; 395– (M–H)–. IR spectrum: Absorptions region ν(NH); 1776, 1758 cm$^{-1}$ ν(C=O); 1678, 1630 cm$^{-1}$ ν(C=O)+ν(COO); 1586, 1501 cm$^{-1}$ amide II+aromatics. Microanalysis:

| Calculated: | Obtained: |
|---|---|
| % C: 60.3% | % C: 60% |
| % H: 6.3% | % H: 6.5% |
| % N: 14.08% | % N: 12.9% |

EXAMPLE 8

2-Propenyl [[1,5-Dihydro-3-oxo-1-[[(phenylsulfonyl)amino]carbonyl]-2,5-methano-2H-1,2,4-benzotriazepin-4(3H)-yl]oxy]acetate 100 mg of the product obtained in example 3 are dissolved in 1 ml of toluene. 63.3 mg of benzenesulfonyl isocyanate are added at 0° C. and the reaction mixture is left stirring under argon at ambient temperature for 45 min. The resulting compound is purified by preparative thin layer chromatography operations (eluent: heptane/AcOEt (2:1)) and 150 mg of the expected product (92%) are isolated.

EXAMPLE 9

Bis[N-(1-methylethyl)-2-propanaminium] salt of [[1,5-dihydro-3-oxo-1-[[(phenylsulfonyl)amino] carbonyl]-2,5-methano-2H-1,2,4-benzotriazepin-4 (3H)-yl]oxy]acetic acid 148 mg of the product obtained in example 8 are dissolved in 1.5 ml of THF. 36 mg of tetrakis(triphenylphosphine) palladium and then 158.4 mg of diisopropylamine are added to the solution. The reaction mixture is left stirring under argon at 0° C. for 20 minutes. 0.1 ml of ether is added and then the precipitate is filtered off. It is washed with 1 ml of a THF/ether (4:1) mixture. 66 mg of the expected product (35%) are isolated.

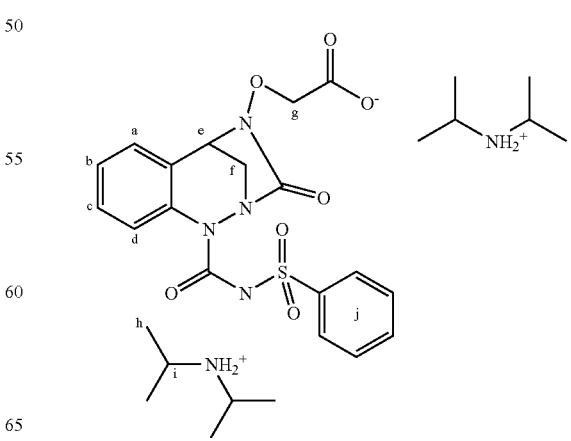

NMR spectrum: (d$_6$-DMSO) 24H: 1.18 ppm (d, J=6.5) Hh; 4H: 3.28 ppm (sept, J=6.5); Hi; 1H: 2.98 ppm (d, J=11.5) Hf1; 1H: 3.44 ppm (dd, J=11.5 and 2.5) Hf2; 1H: 4.94 ppm (d, J=2.5) He; 2H: 4.06 ppm; system of AB type Hg; 1H: 6.84 ppm (td, J=8 and 1.5) Hb; 1H: 7.13 ppm (td, J=8 and 1.5) Hb and Hd; 1H: 7.23 ppm (dd, J=8 and 1.5) Ha, 1H: 8.06 ppm (dd, J=8 and 1.5) Hd; 3H: 7.37 ppm (m) Hj; 2H: 7.78 ppm (m) Hj; <4H: 8.49 ppm (bs) mobile H. Mass spectrum: 433+MH+; 431+MH+. IR spectrum: Absorptions region ν(NH); 1748 c$^{-1}$ ν(C=O)+ν(COO—); 1500 cm$^{-1}$ aromatics.

EXAMPLE 10

Ethyl 4,5-dihydro-α,3-dioxo-4-[2-oxo-2-(2-propenyloxy)ethoxy]-2,5-methano-2H-1,2,4-benzotriazepin-1(3H)-acetate 100 mg of the product obtained in example 3 are dissolved in 4 ml of anhydrous CH$_2$Cl$_2$. 45.4 mg of triethylamine are subsequently added, followed, at 0° C., by 61.37 mg of ethyl chloroglyoxylate and then by 54.8 mg of dimethylaminopyridine. The temperature is allowed to return to ambient temperature. After 15 min, the CH$_2$Cl$_2$ is evaporated and the residue is treated with a heptane:AcOEt 1:1 mixture and NaH$_2$PO$_4$ (1M aqueous solution). After extracting with AcOEt and then washing the organic phase with water and drying over MgSO$_4$, the solvent is evaporated and 124.6 mg of the expected product (93%) are isolated.

EXAMPLE 11

N-(1-Methylethyl)-2-propanaminium salt of [(1,5-dihydro-3-oxo-2,5-methano-2H-1,2,4-benzotriazepin-4(3H)-yl)oxy]acetate acid 80.7 mg of the product obtained in example 10 are dissolved in 0.8 ml of THF. 32.2 mg of tetrakis(triphenylphosphine)palladium and then 141.6 mg of diisopropylamine are added to the solution. The reaction mixture is left stirring under argon at 0° C. for 20 minutes. 0.1 ml of ether is added and then the precipitate is filtered off and washed with 1 ml of a THF/ether (4:1) mixture. 87 mg of the expected product (89%) are isolated.

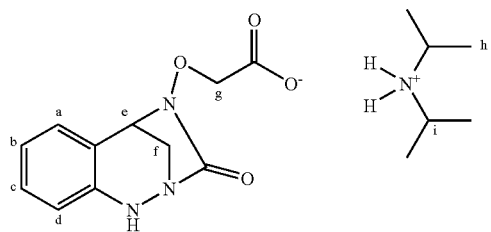

NMR spectrum: (d$_6$-DMSO): 12H: 1.18 ppm (d, J=6.5) Hh; 2H: 3.24 ppm (sept, J=6.5) Hi; 1H: 3.00 ppm (d, J=11) Hf1; 1H: 3.48 ppm (dd, J=11 and 2.5) Hf2; 1H: 4.98 ppm (d, J=2.5) He; 1H: 4.02 ppm (s) Hg; 1H: 6.54 ppm (dd, J=8 and 1) Ha or Hd; 1H: 6.65 ppm (tt) Hd; 1H: 7.11 ppm (td, J=8 and 1.5) Hb and Hc; 1H: 7.15 ppm (dd, J=8 and 1) Ha or Hd; 1H: 8.54 mobile H. Mass spectrum: 351+MH+. IR spectrum: Absorptions region ν(NH) ν(C=O); 1750 cm$^{-1}$ ν(COO—)+aromatics+def. NH—NH$_2$+; 1641, 1607, 1572, 1505 cm$^{-1}$. UV spectrum: 245 nm ε=7200; 288 nm ε=1800. Microanalysis:

| Calculated: | Obtained: |
|---|---|
| % C: 58.3% | % C: 58.4% |
| % H: 7.5% | % H: 7.5% |
| % N: 16% | % N: 15.5% |
|  | % H$_2$O: 0.4% |

EXAMPLE 12

Ethyl 4,5-dihydro-3-oxo-4-(2-propenyloxy)-2,5-methano-2H-1,2,4-benzotriazepine-1(3H)-acetate 500 mg of the product obtained in example 1 are dissolved in 4 ml of DMF. 397.2 mg of ethyl bromoacetate are subsequently added, followed, at 0° C., by 114.1 mg of sodium hydride (50% in oil). After stirring for 20 minutes under argon, the reaction medium is treated with a heptane/AcOEt (1:2) mixture and NaH$_2$PO$_4$ (1M aqueous solution). After extracting with AcOEt and then washing the organic phase with water, the organic phase is dried over MgSO$_4$ and the solvent is evaporated. The residue is chromatographed on silica (eluent: heptane/AcOEt 2:1). 418.4 mg of the expected product (61%) are isolated.

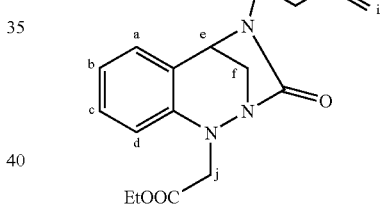

NMR spectrum: (CDCl$_3$): 3H: 1.27 (t, J=7) CH$_3$ of the ethyl; 2H: 4.20 ppm (q, J=7) CH$_2$ of the ethyl; 1H: 4.40 ppm, 1H: 4.47 ppm system of AB type Hj; 1H: 3.52 ppm (d, J=11.5) Hf1; 1H: 3.60 ppm (dd, J=11.5 and 3) Hf2; 1H: 4.40 ppm (d, J=3) He; 2H: 4.42 ppm (masked) Hg; 1H: 6.01 ppm (m) Hh; 1H: 5.31 ppm (bd, J=10.5) Hi1, 1H: 5.35 ppm (dq, J=17 and 1.5) Hi2; 1H: 6.46 ppm (bd, J=8) Hd or Ha; 1H: 7.11 ppm (dd, J=8 and 1.5) Ha or Hd; 1H: 6.76 ppm (bt, J=8), 1H: 7.22 ppm (td, J=8 and 1.5) Hc and Hb. Mass spectrum: 340+MNa+; 318+MH+; 260+M+-(O=C—NH—O—CH$_2$—CH=CH$_2$); 217+little or no =C—NH. IR spectrum: 1767 cm$^{-1}$ ν(C=O) (complex); 1646 cm$^{-1}$ ν(C=C); 1608, 1578 cm$^{-1}$ aromatics. UV spectrum: 250 nm ε=10000; 295 nm ε=2300. Microanalysis:

| Calculated: | Obtained: |
|---|---|
| % C: 62.9% | % C: 63% |
| % H: 7.5% | % H: 7.6% |
| % N: 13.8% | % N: 13.7% |

EXAMPLE 13

4,5-Dihydro-1-methyl-4-(2-propenyloxy)-2,5-methano-2H-1,2,4-benzotriazepin-3(1H)-one 462.5 mg of the product obtained in Example 1 are dissolved in 5 ml of DMF. 567.6 mg of methyl iodide are subsequently added, followed, at 0° C., by 96 mg of sodium hydride (50% in oil). After stirring for 30 minutes under argon, the reaction medium is treated with a heptane/AcOEt (1:2) mixture and $NaH_2PO_4$ (1M aqueous solution). After extracting with AcOEt and then washing the organic phase with water, the organic phase is dried over $MgSO_4$ and the solvent is evaporated. The residue is chromatographed on silica (eluent:heptane:AcOEt 2:1). 392 mg of the expected product (80%) are isolated.

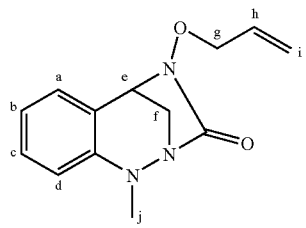

NMR spectrum: ($CDCl_3$): 3H: 3.29 (s) Hj; 1H: 3.23 ppm (d, J=11.5) Hf1; 1H: 3.59 ppm (dd, J=11.5 and 3) Hf2; 1H: 4.37 ppm (d, J=3) He; 2H: 4.41 ppm (bd, J=7) Hg; 1H: 6.01 ppm (m) Hh; 1H: 5.31 ppm (bd, J=10.5) Hi1; 1H: 5.35 ppm (dq, J=11.5 and 1.5) Hi2; 1H: 6.64 ppm (dd, J=8 and 1.5), 1H: 7.07 ppm (dd, J=8 and 1.5) Ha and Hd; 1H: 6.77 ppm (td, J=8 and 1.5), 1H: 7.25 ppm (td, J=8 and 1.5) Hc and Hb. Mass spectrum: 245+M+; 188+M+-(O—$CH_2$—CH=$CH_2$); 145+M+-(NCO—O-All). IR spectrum: 1764 $cm^{-1}$ ν(C=O); 1644 $cm^{-1}$ ν(C=C); 1608, 1576 $cm^{-1}$ aromatics. UV spectrum: 253 nm p=8900; 293 nm ε=2100.

EXAMPLE 14

4,5-Dihydro-4-(2-propenyloxy)-1-(3-pyridinylmethyl)-2,5-methano-2H-1,2,4-benzotriazepin-3(1H)-one 462.5 mg of the product obtained in example 1 are dissolved in 10 ml of DMF. 426.5 mg of 3-chloromethylpyridine hydrochloride are subsequently added, followed, at 0° C., by 113.5 mg of sodium hydride (50% in oil). After stirring for 1 hour under argon, the reaction medium is treated with a heptane/AcOEt (1:1) mixture and $NaH_2PO_4$ (1M aqueous solution). After extracting with AcOEt and then washing the organic phase with water, the organic phase is dried over $MgSO_4$, the solvent is evaporated and the residue is chromatographed on silica (eluent: heptane:AcOEt 3:1). 180 mg of the expected product (28%) are isolated.

EXAMPLE 15

4,5-Dihydro-3-oxo-N-(phenylsulfonyl)-4-(2-propenyloxy)-2,5-methano-2H-1,2,4-benzotriazepin-1(3H)-carboxamide 300 mg of the product obtained in Example 1 are dissolved in 3 ml of toluene. 237.6 mg of benzenesulfonyl isocyanate are added at 0° C. The temperature is allowed to return to ambient temperature. After stirring for 15 min under argon, the crystals are filtered off and washed with toluene. 480 mg of the expected product (89%) are isolated.

EXAMPLE 16

N-Benzoyl-4,5-dihydro-3-oxo-4-(2-propenyloxy)-2,5-methano-2H-1,2,4-benzotriazepine-1(3H)-carboxamide 400 mg of the product obtained in Example 1 are dissolved in 5 ml of toluene. 279.55 mg of benzoyl isocyanate are added at 0° C. The temperature is allowed to return to ambient temperature. After stirring for 30 min under argon, the crystals are filtered off and washed with toluene. 429.4 mg of the expected product (66%) are isolated.

EXAMPLE 17

Ethyl 4,5-dihydro-α,3-dioxo-4-(2-propenyloxy)-2,5-methano-2H-1,2,4-benzotriazepine-1(3H)-carboxamide 400 mg of the product obtained in Example 1 are dissolved in 4 ml of anhydrous $CH_2Cl_2$. 192.1 mg (265 μl) of triethylamine are subsequently added, followed, at 0° C., by 259.8 mg of ethyl chloroglyoxylate and then 232 mg of dimethylaminopyridine. The temperature is allowed to return to ambient temperature. After stirring for 15 min under argon, the $CH_2Cl_2$ is evaporated. The residue is treated with a heptane:AcOEt 1:1 mixture and $NaH_2PO_4$ (1M aqueous solution). After extracting with AcOEt and then washing the organic phase with water and drying over $MgSO_4$, the solvent is evaporated. 556 mg of the expected product (97%) are isolated.

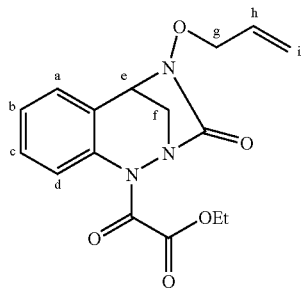

NMR spectrum: ($CDCl_3$): 3H: 1.40 (t, J=7) $CH_3$ of the ethyl; 2H: 4.40 ppm (q, J=7) $CH_2$ of the ethyl; 1H: 3.50 ppm (d, J=12) Hf1; 1H: 3.75 ppm (dd, J=12 and 3) Hf2; 1H: 4.40 ppm (d, J=3) He; 1H: 4.41 ppm (masked) Hg; 1H: 6.01 ppm (m) Hh; 1H: 5.34 ppm (bd, J=10) Hi1; 1H: 5.37 ppm (dq, J=17.5 and 1.5) Hi2; 1H: 7.16 ppm (td, J=8 and 1), 1H: 7.42 ppm (td, J=8 and 1) Hb and Hc; 1H: 7.23 ppm (dd, J=8 and 1) Ha; 1H: 8.40 ppm (dd, J=8 and 1) Hd. Mass spectrum: 332+MH+; 354+MNa+; 395+MNa++$CH_3CN$; 685+(2M+Na)+; 259+MH+-(COOEt); 131+MH+-(COCOOEt)—(CO—N-OAll). IR spectrum: 1794, 1743, 1699 $cm^{-1}$ ν(C=O); 1602, 1582 $cm^{-1}$ aromatics; UV spectrum: 237 nm ε=7700; 260 nm ε=8800; inflection at 276 nm.

EXAMPLE 18

4,5-Dihydro-N-methyl-3-oxo-4-(2-propenyloxy)-2,5-methano-2H-1,2,4-benzotriazepine-1(3H)-sulfonamide 400 mg of the product obtained in Example 1 are dissolved in 5 ml of anhydrous $CH_2Cl_2$. 576 mg of triethylamine are subsequently added at 0° C., followed by 740 mg of methylsulfamoyl chloride. The medium is kept stirred for 20 min. The $CH_2Cl_2$ is evaporated. The residue is treated with a heptane/AcOEt (1:1) mixture and $NaH_2PO_4$ (1M aqueous solution). After extracting with AcOEt and then washing the organic phase with water and drying over $MgSO_4$, the solvent is evaporated. The reaction is repeated with 1.5 eq. of the two above reactants. The compound is subsequently chromatographed on silica (eluent: heptane/AcOEt (2:1)). 226 mg of the expected product (40%) are isolated.

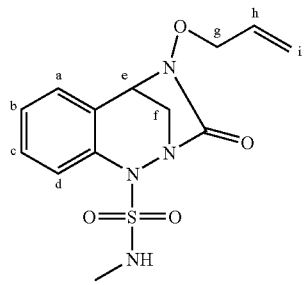

Mass spectrum: 325+MH+; 347+MNa+; 388+MNa++CH$_3$CN; 267+MH+-(—O—CH$_2$—CH=CH$_2$); 232+MH+-(—SO$_2$—NH—CH$_3$); 131+MH+-(CO—N—O—CH$_2$—CH=CH$_2$)—(—SO$_2$—NH—CH$_3$). IR spectrum: 3380 cm$^{-1}$ ν(NH); 1781 cm$^{-1}$ ν(C=O); 1646 cm$^{-1}$ ν(C=C); 1602 cm$^{-1}$ aromatics; 1355, 1175 cm$^{-1}$ ν(SO$_2$). UV spectrum: inflection at 226, 272, 287 nm.

EXAMPLE 19

4,5-Dihydro-3-oxo-N-phenyl-4-(2-propenyloxy)-2,5-methano-2H-1,2,4-benzotriazepine-1(3H)-carbothioamide 40 mg of the product obtained in Example 1 are dissolved in 2 ml of DMF. 25.71 mg of phenyl isothiocyanate are subsequently added at 0° C., followed by 9.129 mg of sodium hydride (50% in oil). The temperature is allowed to return to ambient temperature. After 20 minutes, the medium is treated with a heptane/AcOEt (1:2) mixture and $NaH_2PO_4$ (1M aqueous solution). After extracting with AcOEt and then washing the organic phase with water and drying over $MgSO_4$, the solvent is evaporated. The compound is triturated in ether. 41.5 mg of the expected product (66%) are isolated.

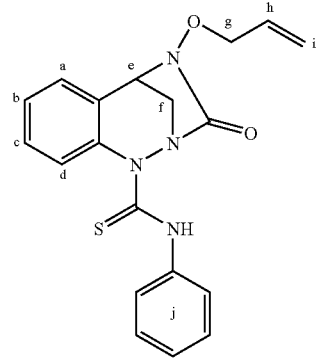

NMR spectrum: (CDCl$_3$): 1H: 3.68 (dd, J=13 and 2) Hf1; 1H: 4.86 ppm (dd, J=13 and 2) Hf2; 1H: 4.43 ppm (t, J=2) He; 2H: 4.22 ppm (m) Hg; 1H: 5.91 ppm (m) Hh; 1H: 5 5.21 ppm (bd, J=10) Hi1; 1H: 5.27 ppm (dq, J=17 and 1.5) Hi2; 1H: 5.52 ppm (bs) mobile H; 1H: 7.31 ppm (td, J=8 and 1), 1H: 7.50 ppm (masked) Hb and Hc; 1H: 7.41 ppm (dd, J=8 and 1) Ha; 1H: 9.28 ppm (dd, J=8 and 1) Hd; 5H: 7.43 and 7.60 ppm (m) Hj. Mass spectrum: 367+MH+; 294+MH+-(—N—O—CH$_2$—CH=CH$_2$); 189+MH+-(O=C—N—O—CH$_2$—CH=CH$_2$)—(Ph); 175+MH+-(CO—N—O—CH$_2$—CH=CH$_2$)—(—NH-Ph). IR spectrum: 3468-3265 cm$^{-1}$ ν(NH); 1745 cm$^{-1}$ ν(C=O); 1646 cm$^{-1}$ ν(C=C); 1605, 1596, 1585, 1494 cm$^{-1}$ aromatics; 1355, 1175 cm$^{-1}$. UV spectrum: 240 nm ε=17400; 311 nm ε=15600.

EXAMPLE 20

4,5-Dihydro-1-(methylsulfonyl)-4-(2-propenyloxy)-2,5-methano-2H-1,2,4-benzotriazepin-3(1H)-one 500 mg of the product obtained in Example 1 are dissolved in 5 ml of anhydrous $CH_2Cl_2$. 545.2 mg of methanesulfonyl chloride are subsequently added at 0° C., followed by 20 480.8 mg of triethylamine and then 581 mg of dimethylaminopyridine. After 30 min, the $CH_2Cl_2$ is evaporated and the residue is treated with a heptane/AcOEt (1:2) mixture and $NaH_2PO_4$ (1M aqueous solution). After extracting with AcOEt and then washing the organic phase with water and drying over $MgSO_4$, the solvent is evaporated. 393.8 mg of the expected product (59%) are isolated.

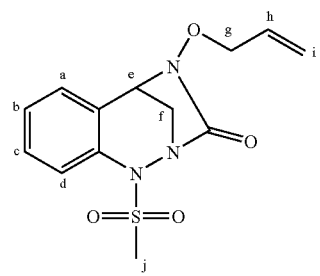

NMR spectrum: (CDCl$_3$): 3H: 3.41 (s) Hj; 1H: 3.63 ppm (d) Hf1; 1H: 3.71 ppm (dd) Hf2; 1H: 4.38 ppm (d) He; 2H:

4.43 ppm (d) Hg; 1H: 6.01 ppm (m) Hh; 1H: 5.35 ppm (d) Hi1; 1H: 5.37 ppm (dq) Hi2; 1H: 7.03 ppm (td) Hb; 1H: 7.34 ppm (td) Hd; 1H: 7.17 ppm (d) Ha; 1H: 7.75 ppm (d) Hd. Mass spectrum: 309+M+; 252+M+-(—O—CH$_2$—CH=CH$_2$); 230+M+-SO$_2$CH$_3$; 210+252+-(N=C=O); 174++M+-(—O—CH$_2$—CH=CH$_2$)—(SO$_2$—CH$_3$); 131 174+-(N=C=O); 103+131+-N$_2$. IR spectrum: Little or no =C—NH; 1790 cm$^{-1}$ ν(C=O); 1645 cm$^{-1}$ ν(C=C); 1603, 1578 cm$^{-1}$ aromatics; probable SO$_2$. Microanalysis:

| Calculated: | Obtained: |
|---|---|
| % C: 50.5% | % C: 62.9% |
| % H: 4.9% | % H: 7.5% |
| % N: 13.6% | % N: 13.8% |
| % S: 10.4% | % S: 10.4% |

EXAMPLE 21

4,5-Dihydro-3-oxo-4-(2-propenyloxy)-2,5-methano-2H-1,2,4-benzotriazepine-1(3H)-carboxamide 500 mg of the product obtained in Example 1 are dissolved in 35 ml of CH$_2$Cl$_2$. 642 mg of triethylamine are subsequently added, followed, at 0° C., by 982.63 mg of diphosgene and, finally, 290 mg of dimethylaminopyridine. The temperature is allowed to return to ambient temperature. After stirring for 20 minutes under argon, a few drops of CH$_2$Cl$_2$ saturated with ammonia are added, the solvent is then evaporated and the residue is then treated with a heptane/AcOEt (1:2) mixture and NaH$_2$PO$_4$ (1M aqueous solution). After extracting with AcOEt and then washing the organic phase with water and drying over MgSO$_4$, the solvent is evaporated. The product, taken up in ether, crystallizes. 286 mg of the expected product (48%) are isolated.

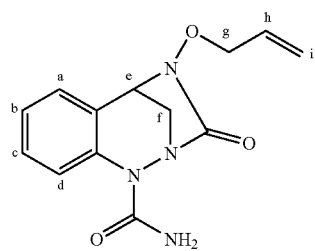

NMR spectrum: (CDCl$_3$): 1H: 3.36 ppm (d, J=11.5) Hf1; 1H: 3.73 ppm (dd, J=11.5 and 3) Hf2; 1H: 4.40 ppm (d, J=3) He; 2H: 4.44 ppm (bd, J=6.5) Hg; 1H: 6.02 ppm (m) Hh; 1H: 5.35 ppm (bd, J=10) Hi1; 1H: 5.37 ppm (dq, J=17 and 1.5) Hi2; 1H: 7.01 ppm (td, J=8 and 1), 1H: 7.35 ppm (td, J=8 and 1) Hb and Hc; 1H: 7.15 ppm (dd, J=8 and 1) Ha; 1H: 8.40 ppm (dd, J=8 and 1) Hd; 1H: 6.52 ppm (st) mobile H; 1H: 4.96 ppm (bs) and 6.96 (bs) mobile NH$_2$. UV spectrum: 241 nm ε=10000; inflection at 277.3 nm. IR spectrum: 3475 cm$^{-1}$ ν(NH); 1774, 1700 cm$^{-1}$ ν(C=O); 1569 cm$^{-1}$ aromatics. Microanalysis:

| Calculated: | Obtained: |
|---|---|
| % C: 56.9% | % C: 56.6% |
| % H: 5.1% | % H: 5.1% |
| % N: 20.4% | % N: 20.4% |

EXAMPLE 22

4,5-Dihydro-3-oxo-N-(phenylmethyl)-4-(2-propenyloxy)-2,5-methano-2H-1,2,4-benzotriazepine-1(3H)-carboxamide 500 mg of the product obtained in Example 1 are dissolved in 220 ml of anhydrous CH$_2$Cl$_2$. 428 mg of triethylamine are subsequently added at 0° C., followed by 436.7 mg of diphosgene and then 290 mg of dimethylaminopyridine. 20 minutes later, 254 mg of benzylamine are added. The temperature is allowed to return to ambient temperature. The CH$_2$Cl$_2$ is evaporated and the residue is treated with a heptane/AcOEt (1:2) mixture and NaH$_2$PO$_4$ (1M aqueous solution). After extracting with AcOEt and then washing the organic phase with water, the organic phase is dried over MgSO$_4$ and the solvent is evaporated. 132 mg of the expected product (17%) are isolated.

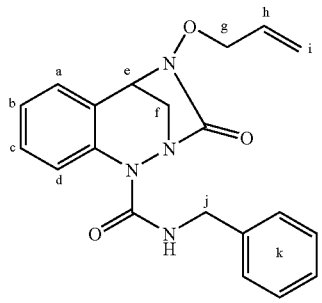

NMR spectrum: (CDCl$_3$): 1H: 3.31 ppm (d, J=11.5) Hf1; 1H: 3.68 ppm (dd, J=1.5 and 3) Hf2; 1H: 4.39 ppm (d, J=3) He; 2H: 4.43 ppm (dd, J=6) Hg; 1H: 6.01 ppm (m) Hh; 1H: 5.33 ppm (d, J=10) Hi1; 1H: 5.36 ppm (dq, J=17 and 1.5) Hi2; 2H: 4.51 ppm (m) Hj; 1H: 7.08 ppm (broad t, J=5.5) mobile NH; 1H: 6.99 ppm (td, J=8.1) Hb; 1H: 7.14 ppm (dd, J=8 and 1) Ha; 6H: 7.27 and 7.40 ppm (m) Hk +Hc; 1H: 8.45 ppm (bd, J=8) Hd. Mass spectrum: 365+MH+; 387+MNa+; 428+MNa+-CH$_3$CN; 751+(2M+Na)+; 322+MH+-(—O—CH$_2$—CH=CH$_2$); 292+MH+-(—N—O—CH$_2$—CH=CH$_2$); 265+MH+-(CO—N—O—CH$_2$—CH=CH$_2$). IR spectrum: 3428 cm$^{-1}$ ν(NH); 1783, 1689 cm$^{-1}$ ν(C=O); 1645 cm$^{-1}$ ν(C=C); 1605, 1585, 1575, 1505 cm$^{-1}$ aromatics. UV spectrum: max. 244 nm ε=12800; infl. 279, 288 nm.

EXAMPLE 23

4,5-Dihydro-1-(phenylmethyl)-4-(2-propenyloxy)-2,5-methano-2H-1,2,4-benzotriazepin-3(1H)-one 300 mg of the product obtained in Example 1 are dissolved in 3 ml of DMF. 180.6 mg of benzyl chloride are added at 0° C., followed by 68.5 mg of sodium hydride (50% in oil). After stirring for 5 minutes at 0° C. under argon, a further 3 ml of DMF are added. After 20 minutes at 0° C., benzyl chloride and sodium hydride are again added (same amounts). After 10 minutes, the reaction medium is treated with a heptane/AcOEt (1:2) mixture and $NaH_2PO_4$ (1M aqueous solution). After extracting with AcOEt and then washing the organic phase with water and drying over $MgSO_4$, the solvent is evaporated. The product is crystallized from ether. 95.8 mg of the expected product (23%) are isolated.

EXAMPLE 24

1,1-Dimethylethyl 4,5-dihydro-3-oxo-4-(2-propenyloxy)-2,5-methano-2H-1,2,4-benzotriazepine-1(3H)-acetate 1.2 g of the product obtained in Example 1 are dissolved in 15 ml of anhydrous DMF. 1.21 g of tert-butyl bromoacetate are subsequently added at 0° C., followed by 271 mg of sodium hydride (50% in oil). The mixture is left at 0° C. for 15 minutes. The reaction medium is treated with a heptane/AcOEt (1:2) mixture and $NaH_2PO_4$ (1M aqueous solution). After extracting with AcOEt and then washing the organic phase with water and drying over $MgSO_4$, the solvent is evaporated. The residue is chromatographed on silica (eluent: heptane/AcOEt 1:2) and 1.52 g of the expected ester (85%) are isolated.

EXAMPLE 25

4,5-Dihydro-3-oxo-4-(2-propenyloxy)-2,5-methano-2H-1,2,4-benzotriazepine-1(3H)-acetic acid The ester obtained in Example 24 is dissolved in 2.5 $cm^3$ of $CH_2Cl_2$ and 7.5 $cm^3$ of trifluoroacetic acid. After 15 min, the solvent is evaporated by entraining it with toluene, and then the compound is crystallized from ether. 519 mg of the expected acid (41%) are obtained.

EXAMPLE 26

4,5-Dihydro-3-oxo-4-(2-propenyloxy)-N-propyl-2,5-methano-2H-1,2,4-benzotriazepine-1(3H)-acetamide 480 mg of the acid obtained in Example 25 are dissolved in 5 ml of DMF. 336.5 mg of 1-hydroxybenzotriazole hydrate and then 350 mg of 1-(3-dimethylaminopropyl)-3-ethylcarbodiimide hydrochloride are added at 0° C. After 20 min at 0° C., 107.9 g of propylamine are added and then the mixture is left at 0° C. for 20 min. The reaction medium is treated with a heptane/AcOEt (1:2) mixture and $NaH_2SO_4$ (1M aqueous solution). After extracting with AcOEt and then washing the organic phase with water, the organic phase is dried over $MgSO_4$ and the solvent is evaporated. The residue is chromatographed on silica (eluent: $CH_2Cl_2$; 6% acetone). 207 mg of the expected product (38%) are isolated.

EXAMPLE 27

Sodium Salt of Ethyl 4,5-dihydro-3-oxo-4-(sulfoxy)-2,5-methano-2-H-1,2,4-benzotriazepine-1(3H)-acetate 410 mg of the product obtained in Example 12 are dissolved in 4 ml of $CH_2Cl_2$. 155.6 mg of acetic acid and then 746 mg of tetrakis(triphenylphosphine)palladium are added to the solution. After stirring for 30 minutes under argon, the solvent is evaporated and the residue is chromatographed on silica (eluent: $CH_2Cl_2$; acetone/$CH_2Cl_2$; acetone/$CH_2Cl_2$+0.1% $NEt_3$ (100 ml)). After evaporating the fractions, 4 $cm^3$ of pyridine and then 764 mg of $SO_3$-pyridine complex are added to the residue, which is left stirring under argon for 2 hours. The 1-propenyltriphenylphosphonium salt of ethyl 4,5-dihydro-3-oxo-4-(sulfooxy)-2,5-methano-2H-1,2,4-benzotriazepine-1(3H)-acetate, in solution in the reaction medium, is obtained. The product is subsequently passed through a Dowex 50*8 resin in the $Na^+$ form, elution being carried out with $H_2O$: 10% THF. The THF is evaporated, the corresponding fractions are lyophilized and, to end, the product is taken up in acetone to remove $Na_2SO_4$ formed. 182 mg of the expected product (37%) are isolated.

EXAMPLE 28

Sodium salt of 4,5-dihydro-1-methyl-4-(sulfooxy)-2,5-methano-2H-1,2,4-benzotriazepin-3(1H)-one 392 mg of the product obtained in Example 13 are dissolved in 4 $cm^3$ of $CH_2Cl_2$. 192 mg of acetic acid and then 924.47 mg of tetrakis(triphenylphosphine)palladium are added to the solution. After stirring for 30 min under argon, 4 $cm^3$ of pyridine and then 764 mg of $SO_3$-pyridine complex are added and the mixture is left stirring under argon for 2 hours. The solvent is evaporated. The expected triphenylphosphonium salt is isolated by chromatography on a silica plate (20% acetone+0.1% triethylamine). The silica comprising the expected product is isolated and the latter is extracted with 25 ml of $CH_2Cl_2$/15% MeOH. The product is subsequently passed through a Dowex 50*8 resin in the $Na^+$ form, elution being carried out with $H_2O$: 10% THF. The THF is evaporated, the corresponding fractions are lyophilized and, to finish, the product is taken up in acetone to remove $Na_2SO_4$ formed. 220 mg of the expected product (45%) are isolated.

NMR spectrum: ($d_6$-DMSO): 3H: 3.16 ppm (s) Hg; 1H: 3.19 ppm (d, J=11.5) Hf1; 1H: 3.54 ppm (dd, J=11.5 and 3) Hf2; 1H: 4.73 ppm (d, J=3) He; 1H: 6.74 ppm (bd, J=8), 1H: 7.05 ppm (dd, J=8 and 1) Ha and Hd; 1H: 6.76 ppm (td, J=8 and 1), 1H: 7.24 ppm (td, J=8 and 1) Hc and Hb. Mass spectrum: 279+$Ph_3P$=O+; 284+MH+; IR spectrum: 3475 $cm^{-1}$ aromatics. UV spectrum (EtOH/HCl): 242 nm $\epsilon$=7300; 296 nm $\epsilon$=1700.

EXAMPLE 29

Sodium salt of 4,5-dihydro-1-(3-pyridinylmethyl)-4-(sulfooxy)-2,5-methano-2H-1,2,4-benzotriazepin-3(1H)-one 170 mg of the product obtained in Example 14 are dissolved in 2 ml of $CH_2Cl_2$. 63.3 mg of acetic acid and then 304.7 mg of tetrakis(triphenylphosphine)palladium are added to the solution. After stirring for 30 min under argon, 2 $cm^3$ of pyridine are added directly to the $CH_2Cl_2$, followed by 246 mg of $SO_3$-pyridine complex, and the mixture is left stirring under argon for 2 hours. The solvent is evaporated and the residue is chromatographed on a silica plate (3% acetone+0.1% triethylamine). The silica comprising the expected product is isolated and the latter is extracted with 25 $cm^3$ of $CH_2Cl_2$/15% MeOH. The product is subsequently passed through Dowex 50W*8 resin in the $Na^+$ form, elution being carried out with $H_2O$: 10% THF. The THF is evaporated, the corresponding fractions are lyophilized and, to finish, the product is taken up in acetone to remove $Na_2SO_4$ formed. 54 mg of the expected product (27%) are isolated.

NMR spectrum: (d6-DMSO): 1H: 3.15 ppm (d, J=11.5) Hf1; 1H: 3.52 ppm (dd, J=11.5 and 2.5) Hf2; 1H: 4.76 ppm (d, J=2.5) He; 1H: 4.64 ppm (d, $J_{AB}$=16) Hg1; 1H: 4.89 ppm (d, $J_{AB}$=16) Hg2; 1H: 6.85 ppm (bd, J=8), 1H: 7.09 ppm (dd, J=8 and 1) Ha and Hd; 1H: 6.78 ppm (td, J=8 and 1), 1H: 7.23 ppm (td, J=8 and 1) Hb and Hc; 7.38 and 8.63 ppm (m) Hh. Mass spectrum: 363+(M'+2H)+; 385$^+$(M'+H+Na); 747+(2M'+2H+Na)+; 361+M+; 723+(2M'+H); 745+(2M'+Na). IR spectrum: Absorption in the region v(NH); 1762 cm$^{-1}$ v(C=O); 1604, 1575 cm$^{-1}$ heterocycle+aromatics.

Pharmacological Study on the Products of the Invention

I/In vitro Antibacterial Activity, Method of Dilutions in Liquid Medium

A series of tubes is prepared, the same amount of sterile nutrient medium being distributed in the tubes. Increasing amounts of the test product are distributed in each tube and then each tube is inoculated with a bacterial strain. After incubating for twenty-four hours in an oven at 37° C., inhibition of growth is assessed by transillumination, which makes it possible to determine the minimum inhibitory concentrations (M.I.C.), expressed in µg/ml.

Tests are thus carried out with the products of Examples 11, 14 and 28.

These compounds have the activities combined in the following table:

|  | MIC, µg/ml, at 24 hours |
|---|---|
| Gram-positive |  |
| S. aureus SG511 | 80-160 |
| S. pyogenes A561 | 40-160 |
| Gram-negative |  |
| E. coli UC1894 | 20-80 |
| E. coli 1507E | 20-160 |
| E. coli DC2 | 20-80 |
| E. cloacae 1321E | 40-80 |

The compounds according to the invention thus show an antibacterial activity.

II/Inhibitory Activity for β-Lactamases

The compounds of formula (I) and their pharmaceutically acceptable salts exhibit marked inhibitory activities against β-lactamases of various bacterial strains and these therapeutically advantageous properties can be determined in vitro with regard to isolated β-lactamases:

A. Preparation of the β-Lactamases Tem-1 and P99

The β-lactamases are isolated from bacterial strains resistant to penicillins and to cephalosporins (Tem1 and P99 are produced respectively by E. coli 250HT21 and E. Cloacae 293HT6).

The bacteria are cultured in 37 g/l brain-heart broth (DIFCO) at 37° C. They are harvested in the exponential phase, cooled and centrifuged. The bacterial pellets are taken up in 50 mM sodium phosphate buffer, pH 7.0, and are again centrifuged. The bacteria are taken up in two volumes of the same buffer and lyzed using a French press maintained at 4° C. After centrifuging for 1 h at 100 000 g at 4° C., the supernatants comprising the soluble fraction of the bacterial extracts are recovered and frozen at −80° C.

B. Determination of the β-Lactamase Activity

The method uses nitrocefin (Oxoid), a chromogenic cephalosporin, the product of hydrolysis by β-lactamases of which is red and absorbed at 485 nm, as substrate. The β-lactamase activity is determined kinetically by the measurement, on a plate spectrophotometer (Spectra Max Plus from Molecular Devices), of the variation in absorbance at 485 nm resulting from the hydrolysis of the substrate. The experiments are carried out at 37° C. The amount of enzyme was standardized and the measurements are carried out at the initial rate.

C. Determination of the Inhibitory Activity for β-Lactamases

Two measurements are carried out, without preincubation and with preincubation of the enzyme and of the inhibitor (5 min), in order to test the irreversibility of the reaction. The products are tested at 6 or 8 concentrations in duplicate. The reaction mixture comprises 100 µM nitrocefin and 50 mM sodium phosphate buffer, pH 7.0.

D. Calculations of the $IC_{50}$ Values

The rates of hydrolysis are measured with and without inhibitor. The concentration of inhibitor which inhibits by 50% the reaction for the hydrolysis of nitrocefin by the enzyme is determined ($IC_{50}$). The processing of the data is carried out using GraFit software (Erathycus Software).

| EXAMPLE No. | $IC_{50}$ nM/TEM1 | $IC_{50}$ nM/P99 |
|---|---|---|
| 5 | $5.7 \times 10^{-4}$ M | $4.6 \times 10^{-4}$ M |
| 7 | $1.1 \times 10^{-4}$ M | $6.3 \times 10^{-5}$ M |
| 9 | $1.6 \times 10^{-4}$ M | $1.8 \times 10^{-4}$ M |
| 11 | $1.4 \times 10^{-5}$ M | $1.5 \times 10^{-5}$ M |
| 14 | $2.6 \times 10^{-5}$ M | $1.7 \times 10^{-5}$ M |
| 15 | $4.5 \times 10^{-4}$ M | $1.1 \times 10^{-4}$ M |
| 27 | $7.5 \times 10^{-6}$ M | $5.3 \times 10^{-7}$ M |
| 28 | $1.2 \times 10^{-5}$ M | $3.7 \times 10^{-5}$ M |

$IC_{50}$ after 5 min of preincubation with the enzyme.

Pharmaceutical Composition Examples:

1) A pharmaceutical composition for injection was prepared, the ingredients of which are as follows:

| compound of example 11 | 500 mg |
|---|---|
| sterile aqueous excipient | q.s. for 10 ml |

2) A pharmaceutical composition (lyophilisate) for injection was prepared, including:

on the one hand: compound of

| on the one hand: compound of example 9 | 500 mg |
|---|---|
| on the other hand: cefotaxime | 1 g |
| sterile aqueous excipient | q.s. for 5 ml |

The two active principles can, if desired, be introduced separately in two separate vials or bottles.

What is claimed is:

1. A compound of formula (I), or a pharmaceutically acceptable salt thereof with a base or acid: in which;

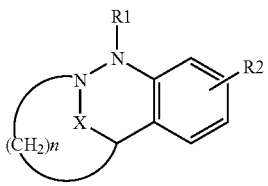

n is 1;
R1 is selected from the group consisting of hydrogen, alkyl having up to 8 carbon atoms and $(CH_2)_{n'}R^o{}_1$ in which n' is 0 or 1 and $R^o{}_1$ is selected from the group consisting of aryl having up to 12 carbon atoms; heteroaryl having up to 15 carbon atoms and at least one heteroatom selected from N, S, and O; COR'; CONR'R"; CSNR'R"; COCOOR'; $SO_2NR'R"$; $SO_2R'$; $CO_2R'$ and CN;
R' is selected from the group consisting of hydrogen, alkyl having up to 8 carbon atoms, alkenyl having up to 8 carbon atoms, aralkyl having up to 12 carbon atoms and aryl having up to 12 carbon atoms;
R" is selected from the group consisting of hydrogen; alkyl having up to 8 carbon atoms; aryl having up to 12 carbon atoms; aralkyl having up to 12 carbon atoms; $SO_2$—R' and COR'; in each case R' being independently selected from the group consisting of hydrogen, alkyl having up to 8 carbon atoms, alkenyl having up to 8 carbon atoms, aralkyl having up to 12 carbon atoms and aryl having up to 12 carbon atoms;
R2 is selected from the group consisting of hydrogen, halo, alkyl, OH, Oalkyl, $NO_2$, $NH_2$, NHalkyl, $N(alkyl)_2$, NHCOalkyl, $NHSO_2$alkyl, CONHalkyl, $SO_2$NHalkyl, COOH, COOalkyl, CN, $OSO_2$alkyl, NHCONHalkyl and COalkyl; said alkyl having up to 8 carbon atoms;
X is a divalent group —C(O)—N(OR$_3$)— connected to the ring nitrogen atom via its carbonyl carbon atom and to the ring carbon atom via its nitrogen atom, in which $R_3$ is selected from the group consisting of hydrogen and the R, Y, $Y_1$, $Y_2$ and $Y_3$ moieties defined below;
R is selected from the group consisting of alkyl having up to 6 carbon atoms, optionally substituted by pyridyl or carbamoyl; alkenyl having up to 8 carbon atoms; aryl having up to 12 carbon atoms; and aralkyl having up to 12 carbon atoms; each said aryl group optionally being substituted by an —OH, —$NH_2$, —$NO_2$, alkyl having up to 8 carbon atoms, an alkoxy having up to 8 carbon atoms or by one or more halogens;
Y is selected from the group consisting of COR, COOH, COOR, CONHR, CONHOH, $CONHSO_2R$, $CH_2COOH$, $CH_2COOR$, $CH_2CONHOH$, $CH_2CONHCN$, $CH_2$tetrazole, $CH_2$(protected tetrazole), $CH_2SO_3H$, $CH_2SO_2R$, $CH_2PO(OR)_2$, $CH_2PO(OR)(OH)$, $CH_2PO(R)(OH)$ and $CH_2PO(OH)_2$, wherein R is as defined hereinabove;
$Y_1$ is selected from the group consisting of $SO_2R$, $SO_2NHCOR$, $SO_2NHCOOR$, $SO_2NHCONHR$ and $SO_3H$, wherein R is as defined hereinabove;
$Y_2$ is selected from the group consisting of $PO(OH)_2$, $PO(OR)_2$, PO(OH)(OR) and PO(OH)(R), wherein R is as defined hereinabove;
$Y_3$ is selected from the group consisting of tetrazole, tetrazole substituted by R, squarate, NRtetrazole, NRtetrazole substituted by R, and $NRSO_2R$, wherein R is as defined above, including the pure enantiomers thereof, in the R, S or RS configuration, as well as any racemic mixture of said enantiomers.

2. A compound as claimed in claim 1, wherein R2 is hydrogen.

3. A compound as claimed in claim 1, wherein R1 is hydrogen, alkyl having up to 8 carbon atoms or $(CH_2)_{n'}R^o{}_1$ wherein n' is 0 or 1 and $R^o{}_1$ is aryl having up to 12 carbon atoms; heteroaryl having up to 15 carbon atoms and at least one heteroatom selected from N, S, and O; CONR'R"; CSNR'R"; COCOOR' $SO_2NR'R"$; $SO_2R'$ or $CO_2R'$; R' and R" being as defined in claim 1.

4. A compound as claimed in claim 1, wherein X is a divalent group —C(O)—N(OR$_3$)— in which $R_3$ is selected from the group consisting of hydrogen and the R, Y and $Y_1$ radicals, R, Y and $Y_1$ being as defined in claim 1.

5. A compound of formula (I) as defined in claim 1, selected from the group consisting of:
[[1,5-dihydro-1-(methylsulfonyl)-3-oxo-2,5-methano-2H-1,2,4-benzotriazepin-4(3H)-yl]oxy]acetic acid,
[[1-[(benzoylamino)carbonyl]-1,5-dihydro-3-oxo-2,5-methano-2H-1,2,4-benzotriazepin-4(3H)-yl]oxy]acetic acid,
[[1,5-dihydro-3-oxo-1-[(phenylsulfonyl)aminocarbonyl]-2,5-methano-2H-1,2,4-benzotriazepin-4(3H)-yl]oxy]acetic acid,
[(1,5-dihydro-3-oxo-2,5-methano-2H-1,2,4-benzotriazepin-4(3H)-yl)oxy]acetic acid,
4,5-dihydro-1-methyl-4-(sulfooxy)-2,5-methano-2H-1,2,4-benzotriazepin-3(1H)-one,
4,5-dihydro-4-(2-propenyloxy)-1-(3-pyridinylmethyl)-2,5-methano-2H-1,2,4-benzotriazepin-3(1H)one,
4,5-dihydro-3-oxo-N-(phenylsulfonyl)-4-(2-propenyloxy)-2,5-methano-2H-1,2,4-benzotriazepine-1(3H)-carboxamide,
N-benzoyl-4,5-dihydro-3-oxo-4-(2-propenyloxy)-2,5-methano-2H-1,2,4-benzotriazepine-1(3H)-carboxamide,
ethyl 4,5-dihydro-α,3-dioxo-4-(2-propenyloxy)-2,5-methano-2H-1,2,4-benzotriazepine-1(3H)-acetate,
ethyl 4,5-dihydro-3-oxo-4-(sulfooxy)-2,5-methano-2H-1,2,4-benzotriazepine-1(3H)-acetate,
and their salts and enantiomers as defined in claim 1.

6. A process for the preparation of a compound as claimed in claim 1, which process comprises: a) a first stage during which a compound of formula (II):

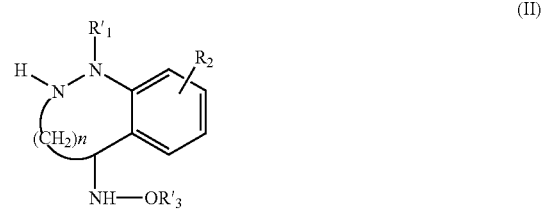

in which:

R'1 is R1, $R_2$ is R2, and R2 and n are as defined in claim 1 and R'$_3$ is selected from the group consisting of a protective group for hydroxyl, Rp, Yp, Y$_1$p, Y$_2$p and Y$_3$p, which, respectively, correspond to R, Y, Y$_1$, Y$_2$ and Y$_3$ as defined in claim 1, in which the possible reactive functional groups present are, if appropriate, protected, is reacted with a carbonylating agent, if appropriate in the presence of a base, for the purpose of obtaining an intermediate compound of formula (III):

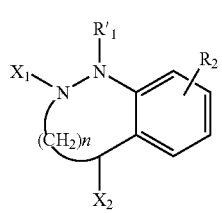

(III)

in which:

R'$_1$ and R$_2$ are defined above, and R2 and n are as defined in claim 1 and either (1) X$_1$ is hydrogen and X$_2$ represents an —N(OR'$_3$)—CO—X$_3$ group, wherein R'$_3$ is as defined above and X$_3$ is the residue of the carbonylating agent, or (2) X$_2$ is —NH—OR'$_3$ and X$_1$ is CO—X$_3$ group, X$_3$ being as defined above;

and b) a second stage during which the intermediate of formula III obtained above is cyclized, in the presence of a base.

7. The process of claim 6 further comprising, either before stage a) or after stage b), as appropriate:
   c) one or more of the following reactions, in an appropriate order:
   protection of the reactive functional groups,
   deprotection of the reactive functional groups,
   esterification,
   saponification,
   sulfonation,
   phosphatation,
   amidation,
   acylation,
   sulfonylation,
   alkylation,
   formation of a urea group,
   introduction of a tetrazole group,
   reduction of carboxylic acids,
   dehydration of amide to nitrile,
   salification,
   exchange of ions,
   separation of enantiomers,
   nitration,
   reduction of a nitro to an amino,
   halogenation,
   carbamoylation,
   introduction of a cyano group.

8. The process as claimed in claim 6, wherein the carbonylating agent is selected from the group consisting of phosgene, diphosgene, triphosgene, aryl, aralkyl, alkyl and alkenyl chloroformates, alkyl dicarbonates, carbonyidiimidazole and their mixtures.

9. The process as claimed in claim 6, wherein the carbonylation reaction takes place in the presence of a base.

10. The process as claimed in claim 6, wherein, in stage b), the base is selected from the group consisting of amines, alkali metal hydrides, alkoxides, amides and carbonates and alkaline earth metal hydrides, alkoxides, amides and carbonates.

11. The process as claimed in claim 10, wherein the base is an amine.

12. The process as claimed in claim 6, wherein the compound of formula (II) is obtained by a process wherein a compound of formula (IV):

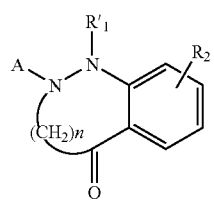

(IV)

in which R'$_1$ and R$_2$ are as defined in claim 6, R2 is selected from the group consisting of hydrogen, halo, alkyl, OH, Oalkyl, NO$_2$, NH$_2$, NHalkyl, N(alkyl)$_2$, NHCOalkyl, NHSO$_2$alkyl, CONHalkyl, SO$_2$NHalkyl, COOH, COOalkyl, CN, OSO$_2$alkyl, NHCONHalkyl and COalkyl; said alkyl having up to 8 carbon atoms and n is 1, and A is hydrogen or a protective group for the nitrogen, is treated with a reducing agent, to obtain a compound of formula (V):

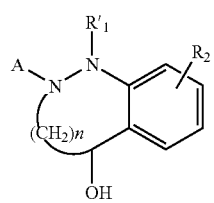

(V)

in which A is defined above, R'$_1$ and R$_2$ are as defined in claim 6, and R2 and n are as defined above, and in which process, if appropriate, the OH group is replaced by a leaving group, to obtain a compound of formula (VI):

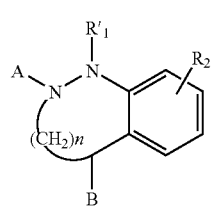

(VI)

in which A is defined above, $R'_1$ and $R_2$ are as defined in claim 6, and R2 and n are as defined above, and B represents a leaving group, which compound of formula VI is then treated with a compound of formula $NH_2$—$OR'_3$, $R'_3$ being as defined in claim 6, and then, if appropriate, with an appropriate deprotecting agent for the nitrogen atom.

13. The process as claimed in claim 12, wherein the compound of formula (II) is obtained by a process wherein a compound of formula (IV) as defined in claim 12 is treated with a compound of formula $H_2N$—$OR'_3$, to obtain a compound of formula (VII):

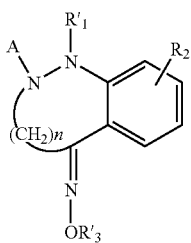

(VII)

in which A is as defined in claim 12, and $R'_1$ and $R_2$ are as defined in claim 12, and R2 and n are as defined in claim 12, and $R'_3$ is as defined in claim 12, which compound of formula VII is then reacted with a reducing agent, to obtain a compound of formula (VIII):

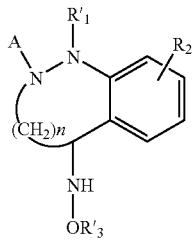

(VIII)

in which A is as defined in claim 12, $R'_1$ and $R_2$ are as defined in claim 12, and R2 and n are as defined in claim 12, and $R'_3$ is as defined in claim 12, which compound of formula VIII is then treated, if appropriate, with an appropriate deprotecting agent for the nitrogen atom.

14. A pharmaceutical composition comprising the compound as defined in claim 1 in combination with a pharmaceutically acceptable carrier.

15. A pharmaceutical composition comprising the compound as defined in claim 5 in combination with a pharmaceutically acceptable carrier.

16. A method of treating a bacterial infection in a mammal comprising administering to a mammal in need thereof an antibacterially effective amount of a compound of claim 1.

17. A method of treating an infection in a mammal that is due to the presence of bacteria that generate beta-lactamases, which comprises administering to a mammal in need thereof an amount of a compound of claim 1 that is effective to inhibit the generation of beta-lactamases by the bacteria in said mammal.

* * * * *